(12) United States Patent
Kitajima et al.

(10) Patent No.: US 8,126,526 B2
(45) Date of Patent: Feb. 28, 2012

(54) PULSE WAVE ANALYZING DEVICE

(75) Inventors: Kazumi Kitajima, Higashiosaka (JP); Koji Yamamoto, Kawanishi (JP); Koichi Terauchi, Toyohashi (JP)

(73) Assignee: Konica Minolta Sensing, Inc. (JP)

( * ) Notice: Subject to any disclaimer, the term of this patent is extended or adjusted under 35 U.S.C. 154(b) by 849 days.

(21) Appl. No.: 11/590,632

(22) Filed: Oct. 31, 2006

(65) Prior Publication Data

US 2007/0118028 A1 May 24, 2007

(30) Foreign Application Priority Data

Oct. 31, 2005 (JP) .................................. 2005-316583

(51) Int. Cl.
*A61B 5/1455* (2006.01)
*A61B 5/02* (2006.01)
(52) U.S. Cl. ........................................ 600/324; 600/500
(58) Field of Classification Search .................. 600/323, 600/324, 326
See application file for complete search history.

(56) References Cited

U.S. PATENT DOCUMENTS

| | | | |
|---|---|---|---|
| 6,151,516 A * | 11/2000 | Kiani-Azarbayjany et al. .......................... | 600/322 |
| 2002/0037533 A1* | 3/2002 | Civelli et al. ................. | 435/7.1 |
| 2003/0009107 A1* | 1/2003 | Kawada et al. .............. | 600/516 |
| 2003/0181798 A1* | 9/2003 | Al-Ali .......................... | 600/324 |
| 2003/0236647 A1* | 12/2003 | Yoon et al. .................... | 702/183 |
| 2004/0220483 A1* | 11/2004 | Yeo et al. ...................... | 600/500 |
| 2005/0033128 A1* | 2/2005 | Ali et al. ....................... | 600/323 |
| 2005/0131283 A1* | 6/2005 | Grant et al. ................... | 600/323 |
| 2005/0234312 A1* | 10/2005 | Suzuki et al. ................. | 600/300 |
| 2005/0234317 A1* | 10/2005 | Kiani ............................ | 600/323 |

FOREIGN PATENT DOCUMENTS

| JP | 2005-110920 A | 4/2005 |
|---|---|---|
| JP | 2005-115799 A | 4/2005 |

OTHER PUBLICATIONS

Japanese Notice of Reasons for Rejection dated Oct. 19, 2010, for counterpart Japanese Application No. 2005-316583, together with an English translation thereof.

\* cited by examiner

*Primary Examiner* — Eric Winakur
(74) *Attorney, Agent, or Firm* — Cantor Colburn LLP

(57) ABSTRACT

A pulse wave analyzing device is provided with a performance part for performing analyzing of a pulse wave of a living body; and a mounting member for substantially integrally mounting constituent elements of the performance part. The performance part includes: a sensor section for measuring parameters relating to the pulse wave of the living body; an A/D converter for converting a measurement signal outputted from the sensor section into a digital signal; an analysis processing section for performing a predetermined data analysis with respect to measurement data outputted from the A/D converter; and a display section for displaying predetermined information relating to the measurement. The analysis processing section has a first analysis processor for performing a pulse wave analysis at least for a first case, and a second analysis processor for performing a pulse wave analysis for a second case different from the first case based on the measurement data relating to the pulse wave.

25 Claims, 24 Drawing Sheets

(NORMAL HEALTHY PERSON)

(ATRIAL FIBRILLATION PATIENT)

(EXTRASYSTOLIC ARRHYTHMIA PATIENT)

FIG.15

| AMPLITUDE | 0~0.025 | 0.025~0.04 | 0.04~0.06 | 0.06~0.08 | 0.08~0.10 |
|---|---|---|---|---|---|
| SLEEP CONDITION | REM SLEEP | Stage1 | Stage2 | Stage3 | Stage4 |

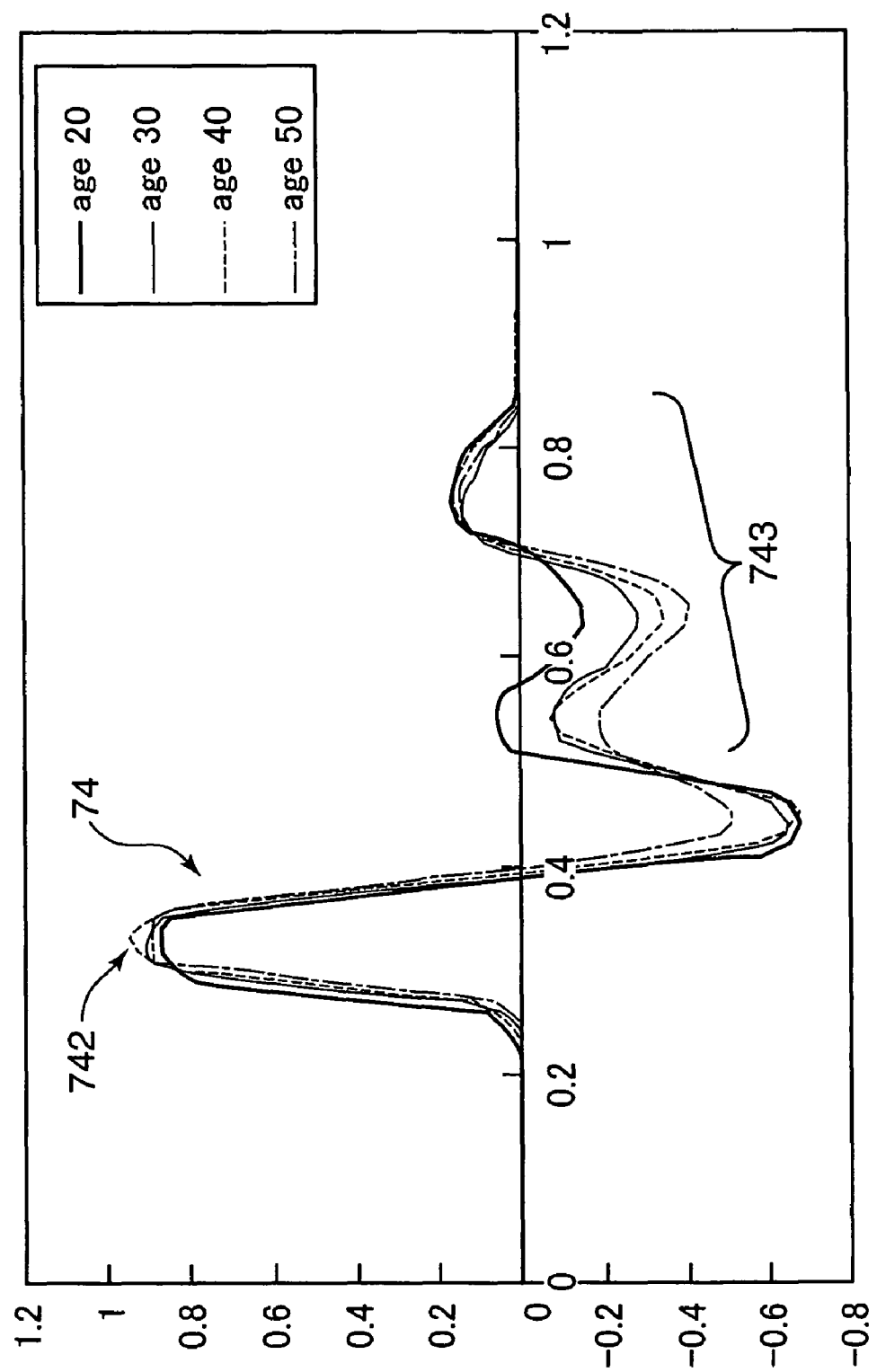

PULSE WAVE ANALYZING DEVICE

This application is based on Japanese Patent Application No. 2005-316583 filed on Oct. 31, 2005, the contents of which are hereby incorporated by reference.

BACKGROUND OF THE INVENTION

1. Field of the Invention

The present invention relates to a pulse wave analyzing device that enables to measure parameters relating to a pulse wave of a living body and to provide a broad-ranging analysis concerning obtained measurement data so as to acquire findings on different cases concerning diseases (hereinafter, simply called as "cases").

2. Description of the Related Art

There are known, for instance, a pulse oximeter, a polysomnography (PSG), and a holter monitor, as examples of a vital information measuring device for non-invasively detecting vital information concerning a living body such as a human body. The pulse oximeter is primarily used for diagnosing a sleep apnea syndrome (SAS), and is adapted to obtain a time-based change in blood oxygen saturation ($SpO_2$) based on a two-wavelength pulse oximetry, which is conducted by: removably attaching a probe provided with a light emitter of emitting light of two different wavelengths and a light detector onto a finger of a subject; projecting light from the light emitter onto a living body i.e. the finger of the subject; and detecting a change in the amount of light transmitted through the living body. The PSG is a measuring device used in diagnosing SAS, as well as the pulse oximeter. The PSG is provided with sensor sections for detecting assessment parameters such as an electroencephalogram, an air flow rate through mouth or nose, snoring sounds, body positions/body movements, chest and abdominal movements in respiration, and electrocardiographic waveform, in addition to the $SpO_2$, to analyze and display the measurement results. The holter monitor is a measuring device for diagnosing an arrhythmia or an atrial fibrillation. The holter monitor is provided with electrodes for detecting a cardiac activity potential, and is adapted to obtain electrocardiogram RR-intervals by analyzing an electrocardiographic waveform.

There is also known a portable vital information monitoring device capable of monitoring vital information without the need of replacing the device during sleep and during waking hours. The portable vital information monitoring device detects vital information which reflects pulsations, body movements, and an autonomic nervous system of a subject to constantly monitor vital information concerning the subject based on an assessment index during sleep and an assessment index during waking hours.

The conventional vital information measuring devices such as the pulse oximeter, the PSG, and the holter monitor are operated in such a manner that measurement data obtained by a measuring operation is temporarily stored in a memory section provided in the vital information measuring devices, and then, the measuring devices are connected to a personal computer with an analysis software or a like device to read the measurement data out of the memory section for data analysis. With use of the conventional measuring devices, the subject cannot be promptly informed of an analysis result concerning a case. Even with use of a measuring device easily measurable at home, the subject is requested to bring the measuring device to a medical institute after the measurement for data analysis to know his or her health condition, which is inconvenient.

Also, use of the conventional measuring devices is changed depending on cases in such a manner that the pulse oximeter or the PSG is used for a subject with a suspected sleep disorder, and a holter monitor is used for a subject with a suspected circulatory system disease such as an arrhythmia. Accordingly, if a subject has both symptoms related to a sleep disorder and a circulatory system disease, it is extremely difficult to find a symptom on the circulatory system disease based on measurement data obtained by the pulse oximeter, for instance. The portable vital information monitoring device is operable to change a measurement mode or an analysis timing depending on a judgment as to whether a body movement has been detected. However, the portable vital information monitoring device is a measuring device based on a premise that data concerning body movements be acquired, and is not a measuring device capable of providing a broad-ranging analysis on cases solely based on pulse wave data.

SUMMARY OF THE INVENTION

In view of the above problems residing in the conventional examples, it is an object of the present invention to provide a pulse wave analyzing device that enables to acquire measurement data concerning a pulse wave of a living body, and to provide a broad-ranging data analysis for different cases based on the measurement data for display of the analysis results.

An aspect of the invention is directed to a pulse wave analyzing device comprising: a performance part for performing analyzing of a pulse wave of a living body; and a mounting member for substantially integrally mounting constituent elements of the performance part. The performance part includes: a sensor section for measuring a parameter relating to the pulse wave of the living body; an A/D converter for converting a measurement signal outputted from the sensor section into a digital signal; an analysis processing section for performing a predetermined data analysis with respect to measurement data outputted from the A/D converter; and a display section for displaying predetermined information relating to the measurement, wherein the analysis processing section has a first analysis processor for performing a pulse wave analysis at least for a first case, and a second analysis processor for performing a pulse wave analysis for a second case different from the first case based on the measurement data relating to the pulse wave.

These and other objects, features and advantages of the present invention will become more apparent upon reading the following detailed description along with the accompanying drawing.

BRIEF DESCRIPTION OF THE DRAWING

FIGS. 10A through 10C are diagrams showing examples in diagnosing an arrhythmia in terms of trend graph concerning pulse wave peak-to-peak intervals, wherein FIG. 10A is a trend graph of a normal healthy person, FIG. 10B is a trend graph of an atrial fibrillation patient, and FIG. 10C is a trend graph of an extrasystolic arrhythmia patient.

FIGS. 12A and 12B are histograms concerning pulse wave peak-to-peak intervals, wherein FIG. 12A is a histogram typically observed while a normal healthy person is in a normal condition i.e. in a less stressful condition, and FIG. 12B is a histogram typically observed while the normal healthy person is in a highly stressful condition.

FIG. 15 is a diagram showing a sleep condition assessment table, wherein bottom-to-peak amplitude values and sleep conditions are correlated to each other.

FIG. 16 is a graph showing typical characteristics on an acceleration pulse waveform per heartbeat based on generations.

DETAILED DESCRIPTION OF THE PREFERRED EMBODIMENTS

Figure 1:
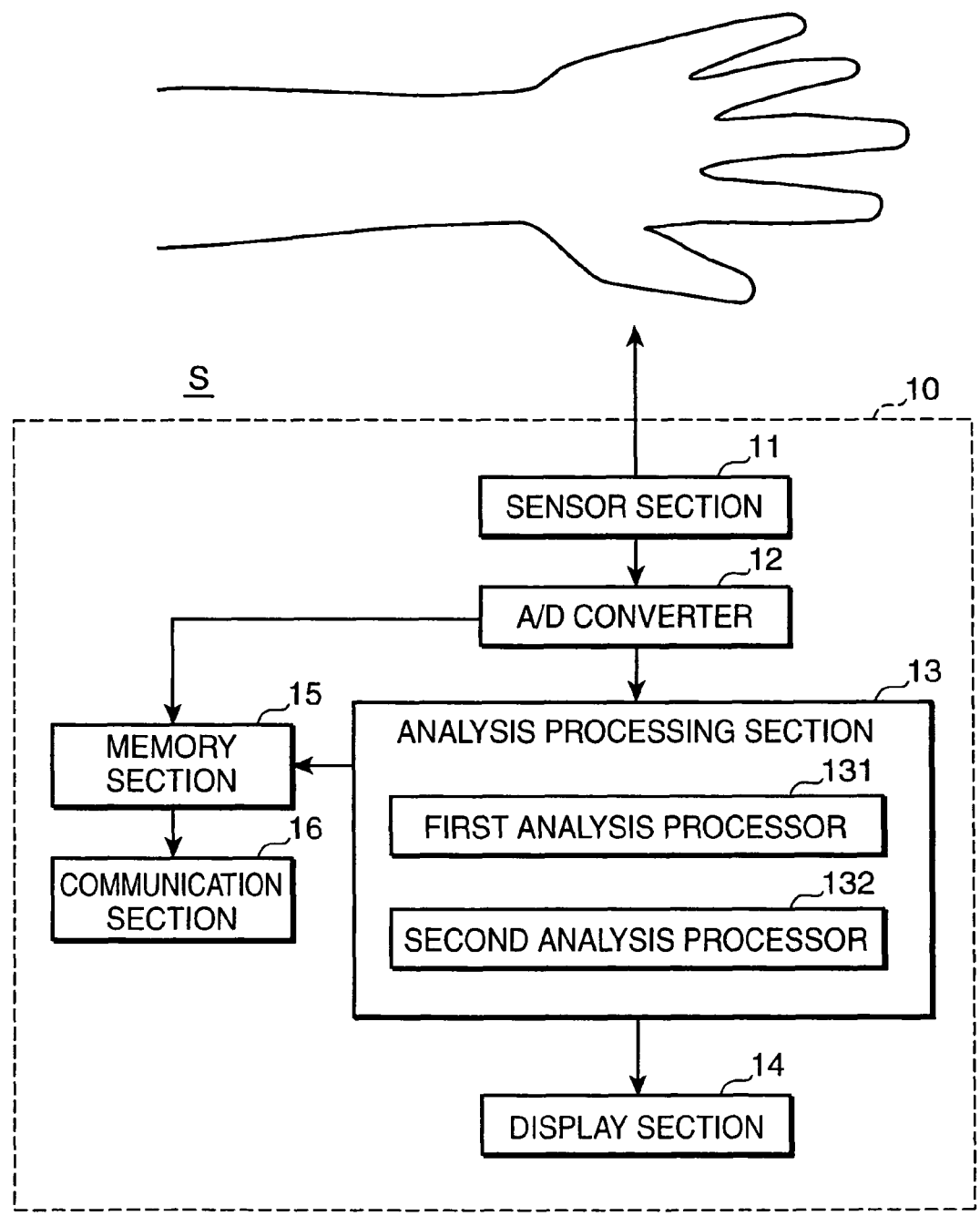
FIG. 1 is a block diagram schematically showing a construction of a pulse wave analyzing device embodying the invention.

In the following, an embodiment of the invention is described referring to the drawings.

Description on Basic Embodiment

FIG. 1 is a block diagram schematically showing a construction of a pulse wave analyzing device "S" embodying the invention. The pulse wave analyzing device "S" includes a performance part, and a device body 10 as a mounting member. Specifically, the performance part including a sensor section 11 for measuring parameters relating to a pulse wave of a living body, an A/D converter 12 for converting an analog measurement signal outputted from the sensor section 11 into a digital signal, an analysis processing section 13 for performing a predetermined data analysis with respect to measurement data outputted from the A/D converter 12, a display section 14 for displaying predetermined information relating to the measurement, a memory section 15 for storing therein measurement data outputted from the A/D converter 12 or measurement data after the analysis by the analysis processing section 13, and a communication section 16 for communicating data with another electrical device such as a personal computer are integrally mounted on the device body 10.

The device body 10 includes a casing member in which the performance part is housed, or a single flexible substrate on which the performance part is mounted, or a like member. It is not necessary that all the constituent elements of the performance part are completely housed in the casing member i.e. the device body 10, or completely mounted on the flexible substrate i.e. the device body 10. For instance, a probe or a like member constituting a part of the sensor section 11 may be withdrawable from the device body 10 via a cable.

The sensor section 11 is not specifically limited, as far as the sensor section 11 is capable of measuring parameters relating to a pulse wave of a subject. Accordingly, various sensing elements may be used. For instance, in the case of measuring a photoelectric pulse wave, a light emitting device such as an LED, and a light detecting device such as a silicon light receiving device may be used as a sensing element. In the case of measuring a blood oxygen saturation ($SpO_2$) as well as the photoelectric pulse wave, a two-wavelength LED may be used as the light emitting device. Further alternatively, a pressure pulse wave detecting system of detecting a pulsation in terms of a movement or a pressure may be used in place of the photoelectric pulse wave detecting system. In addition to the sensing element for measuring a pulse wave, an acceleration sensor for measuring body positions/body movements, chest and abdominal movements in respiration, electrodes for detecting an activity potential of a cardiac muscle, a temperature sensor for measuring an air flow rate through mouth or nose i.e. respiratory movements, or a lavaliere microphone for detecting snoring sounds may be additionally provided as sensing elements.

The A/D converter 12 includes a general-purpose analog-to-digital converting circuit, and converts an analog measurement signal outputted from the sensor section 11 into a predetermined digital signal. Providing the A/D converter 12 allows for storing the analog measurement signal outputted from the sensor section 11 as a digital signal capable of easy computation into the memory section 15, or enables computation in the analysis processing section 13.

The analysis processing section 13 includes a CPU (Central Processing Unit), and performs a predetermined data analysis with respect to the measurement data acquired by the sensor section 11. The analysis processing section 13 includes a first analysis processor 131 for performing a pulse wave analysis for a first case, and a second analysis processor 132 for performing a pulse wave analysis for a second case different from the first case based on the measurement data obtained by the aforementioned process. The cases to be analyzed by the first analysis processor 131 and the second analysis processor 132 may be arbitrarily set. For instance, the first analysis processor 131 may perform an analysis to obtain a sleep apnea index as a first case, and the second analysis processor 132 may perform an analysis to recognize a condition of occurrence of an arrhythmia as the second case.

In this embodiment, the sensor section 11 measures photoelectric pulse wave data based on light of two wavelengths (hereinafter, called as "2-wavelength photoelectric pulse wave data"), which is stored in the memory section 15 in association with time information. The first analysis processor 131 executes a computation of obtaining a sleep apnea index by e.g.: obtaining an instantaneous $SpO_2$ value at each sampling timing to develop the $SpO_2$ values along a time axis and to analyze the change in $SpO_2$ value with time, using the obtained 2-wavelength photoelectric pulse wave data; counting the number of appearances of Dip, which is a peak where the $SpO_2$ value is lowered than a predetermined value e.g. 90%; and calculating the number of appearances of Dip per unit time. The second analysis processor 132 generates a photoelectric pulse waveform, using photoelectric pulse wave data based on light of one wavelength (hereinafter, called as "1-wavelength photoelectric pulse wave data) out of the 2-wavelength photoelectric pulse wave data, obtains peak-to-peak intervals of the 1-wavelength photoelectric pulse waveform, i.e., pulse wave peak-to-peak intervals, and executes a computation of calculating an assessment index for an arrhythmia.

The configuration of the analysis processing section 13 is not limited to the above. The analysis processing section 13 may have plural analysis processors to perform analyses for various cases. For instance, the analysis processing section may be configured to perform analyses for three or more cases. The pulse waveform analyzing method may be arbitrarily set. A method other than the above may be used to obtain a sleep apnea index or to analyze an arrhythmia.

Examples of the display section 14 are an LED display device, a liquid crystal display device, and a CRT (Cathode Ray Tube) display device. An analysis result obtained by the analysis processing section 13 i.e. the first analysis processor 131 and the second analysis processor 132 is displayed in the form of an appropriate indication such as lighting/blinking information, or text, numeral, symbol, pictorial, or character information. The display section 14 selectively or simultaneously displays the analysis results by the first analysis processor 131 and the second analysis processor 132 depending on a detection condition. Preferably, the display manner of the display section 14 may be switched over between a first display mode of displaying the analysis result in detail, and a second display mode of displaying the analysis result in a simplified manner, for instance.

The memory section 15 may include an ROM (Read Only Memory) for storing a control program of the pulse wave analyzing device "S" or the like, an EEPROM (Electrically Erasable Programmable ROM) for temporarily storing data relating to a computation process or a control process, and an involatile memory such as a flash memory so that pulse-wave-related measurement data acquired by the sensor section 11 is stored in the memory section 15 in association with time information, or that measurement data i.e. analysis data after the analysis by the analysis processing section 13 is stored in the memory section 15.

The communication section 16 is an interface device for enabling data communication with another electrical device in transferring the measurement data recorded in the memory section 15 to the another electrical device.

An exemplified operation of the pulse wave analyzing device "S" having the above arrangement is briefly described. When a measurement is started, the sensor section 11 measures information concerning a pulse wave of a subject at each predetermined sampling frequency, and outputs measurement data. The measurement data is converted into a digital signal by the A/D converter 12, and the digital signal is stored in the memory section 15 in association with time information. The measurement operation is cyclically repeated during a measurement period, and the measurement data is accumulated in the memory section 15. If a case requires a real-time measurement analysis, the measurement data is directly outputted to the analysis processing section 13.

After the measurement is completed, the analysis processing section 13 reads the measurement data out of the memory section 15 in response to receiving a command signal from an unillustrated operating section, and then, the first analysis processor 131 and/or the second analysis processor 132 executes a predetermined data analysis process. For example, the first analysis processor 131 executes an analysis to obtain a sleep apnea index and/or the second analysis processor 132 analyzes an arrhythmia. Alternatively, the analysis processing section 13 may perform a real-time data analysis upon receiving a real-time measurement result from the sensor section 11. Thereafter, the data analysis results are displayed on the display section 14 in the form of an appropriate indication.

With the pulse wave analyzing device "S" having the above arrangement, the analysis processing section 13 is enabled to perform data analyses relating to diagnoses of plural cases by one-time measurement of parameters relating to the pulse wave, and the display section 14 is enabled to display the analysis results promptly after the measurement. Thus, the subject himself or herself can readily recognize plural suspected diseases, if any. This provides enhanced convenience, and is advantageous in diagnosing both symptoms on a sleep disorder and a circulatory system disease by one-time measurement even if the subject with suspected symptoms on the sleep disorder and the circulatory system disease visits a clinic for diagnosis.

Description on Pulse Oximeter as Embodiment

Figure 2:
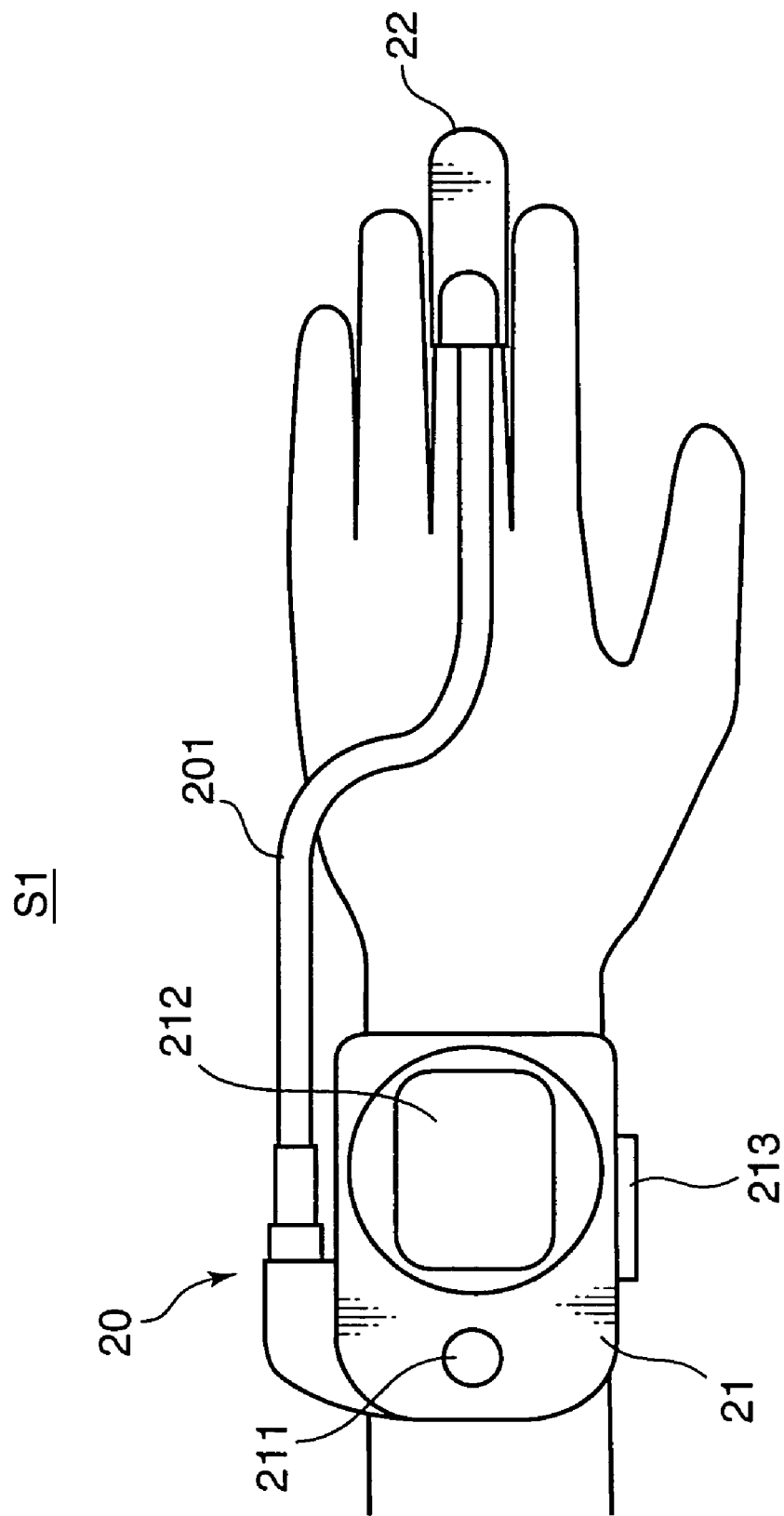
FIG. 2 is a diagram showing an external appearance of a pulse oximeter as an example of the pulse wave analyzing device embodying the invention.

In this section, an embodiment in which the invention is applied to a pulse oximeter capable of measuring $SpO_2$ is described. FIG. 2 is a diagram showing an external appearance of a pulse wave analyzing device "S1" provided with a pulse oximeter 20. A performance part provided with elements corresponding to the sensor section 11, the A/D converter 12, the analysis processing section 13, the display section 14, the memory section 15, and the communication section 16 shown in FIG. 1 is integrally mounted on the pulse oximeter 20. The pulse oximeter 20 includes a device body 21, corresponding to the device body 10 shown in FIG. 1, which is removably attachable to a site near a wrist of a subject, and a probe 22 which is removably attachable to a finger of the subject. The device body 21 and the probe 22 are electrically connected by a single cable 201.

The device body 21 is provided with a power source switch 211, a display section 212 with an LCD or a like device, corresponding to the display section 14, and a belt locking portion 213. Electric circuits serving as the performance part, and electronic components are housed in the device body 21. A light emitting device and a light detecting device constituting a part of the sensor section 11 are provided in the probe 22.

Description on Electrical Configuration

Figure 3:
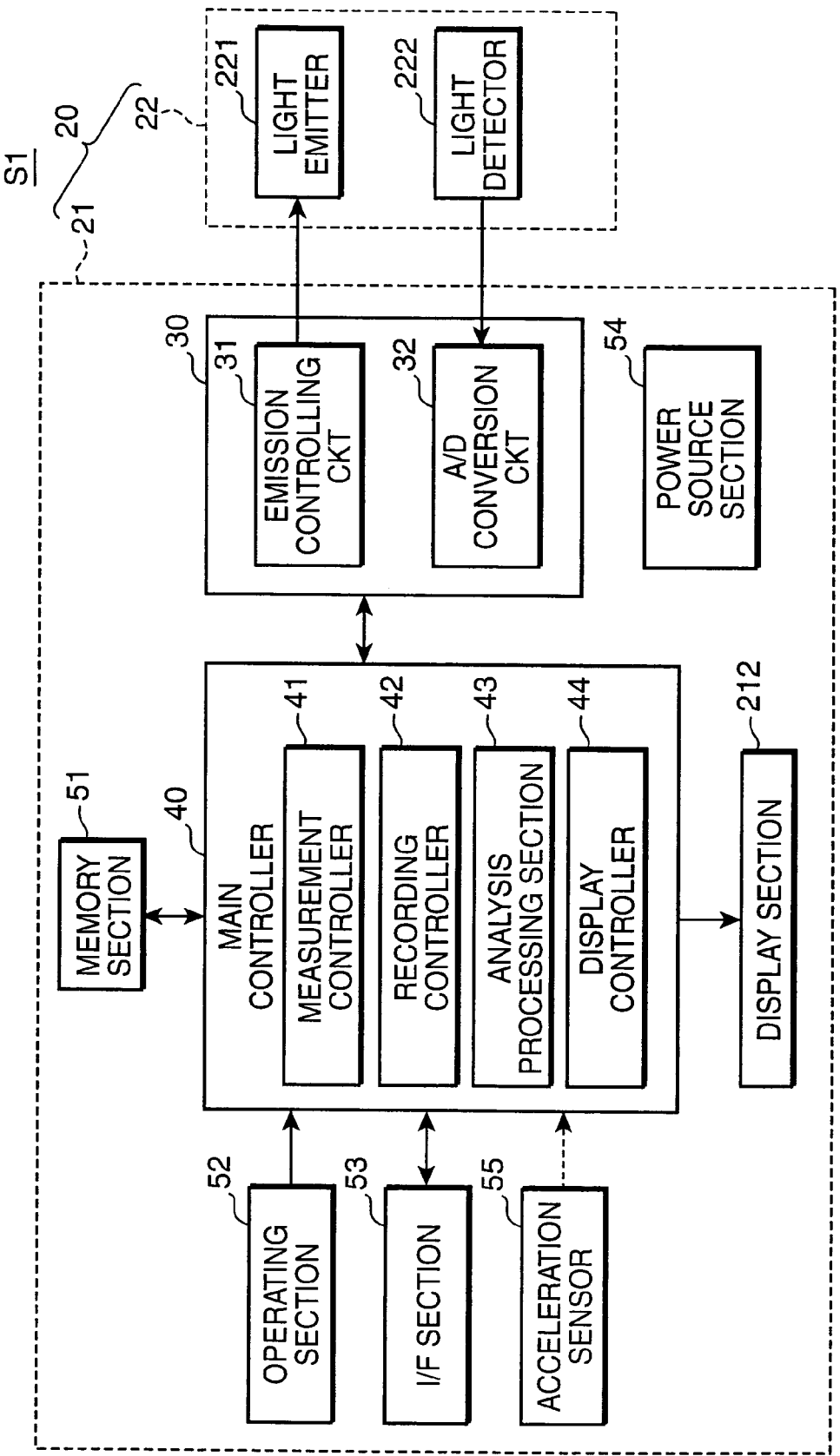
FIG. 3 is a block diagram showing an electric configuration of the pulse oximeter.

FIG. 3 is a block diagram showing an electrical configuration of the pulse oximeter 20. The probe 22 of the pulse oximeter 20 is provided with a light emitter 221 and a light detector 222, as parts of the sensor section. The device body 21 is provided with, in addition to the display section 212, a measurement circuit section 30 serving as a part of the sensor section, a main controller 40 as an analysis processing section, a memory section 51, an operating section 52, an I/F section 53 as a communication section, a power source section 54, and an acceleration sensor 55.

The light emitter 221 includes LEDs for generating light of two wavelengths $\lambda 1$ and $\lambda 2$ different from each other, for instance, a red LED for generating red light of the wavelength $\lambda 1$ in a red color region, and an infrared LED for generating infrared light of the wavelength $\lambda 2$ in an infrared region. The light detector 222 includes a photoelectric conversion device for receiving the light from the light emitter 221 to generate a current commensurate with the intensity of the received light. An example of the photoelectric conversion device is a light detecting device such as a silicon photodiode having photosensitivity to at least the light of the wavelengths $\lambda 1$ and $\lambda 2$.

The light emitter 221 and the light detector 222 may be disposed opposite to each other so that a living tissue e.g. a fingertip of the subject through which $SpO_2$ or 1-wavelength photoelectric pulse wave data is to be measured is securely held therebetween so as to detect the light transmitted through the living body, or may be disposed adjacent to each other to detect the light reflected from the living body. With this arrangement, the light of the wavelength $\lambda 1$ and the light of the wavelength $\lambda 2$ which are emitted from the light emitter 221 are detected by the light detector 222 through the living body so as to acquire 2-wavelength photoelectric pulse wave data. The 2-wavelength photoelectric pulse wave data is necessary to measure the $SpO_2$ i.e. to diagnose a sleep apnea index. However, the 1-wavelength photoelectric pulse wave data may be sufficient to diagnose a case other than SAS. Accordingly, received light data derived from the red LED or the infrared LED is used as the 1-wavelength photoelectric pulse wave data.

The measurement circuit section 30 includes an emission controlling circuit 31 to be connected to the light emitter 221, and an A/D conversion circuit 32 to be connected to the light detector 222. The emission controlling circuit 31 controls the red LED and the infrared LED of the light emitter 221 to alternately emit light based on an emission control signal issued from a measurement controller 41 of the main controller 40, which will be described later, at a predetermined sampling frequency. By the control, red light of the wavelength $\lambda 1$ and infrared light of the wavelength $\lambda 2$ are alternately emitted from the light emitter 221. Similarly to the emission controlling circuit 31, the measurement controller 41 controls the A/D conversion circuit 32 to acquire a photoelectric conversion signal i.e. a measurement signal outputted from the light detector 222 in synchronism with the light emission by the light emitter 221, to convert the measurement signal into a digital signal, and to output the digital signal to the main controller 40.

Oxygen is transported by oxidation/reduction of hemoglobin in the blood. The hemoglobin has such optical characteristics that absorption of red light of the wavelength $\lambda 1$ is decreased, and absorption of infrared light of the wavelength $\lambda 2$ is increased when the hemoglobin is oxidized, and, conversely, absorption of red light of the wavelength $\lambda 1$ is increased and absorption of infrared light of the wavelength $\lambda 2$ is decreased when the hemoglobin is reduced. The probe 22 and the measurement circuit section 30 are designed to utilize the optical characteristics. It is possible to obtain the $SpO_2$ by measuring a variation in transmitted amounts of the red light of the wavelength $\lambda 1$ and the infrared light of the wavelength $\lambda 2$, which are detected by the light detector 222.

The main controller 40 includes a CPU, and controls operations of the respective elements accommodated in the device body 21. The main controller 40 is provided with the measurement controller 41, a recording controller 42, an analysis processing section 43, and a display controller 44.

The measurement controller 41 controls measurement operations to be implemented by the light emitter 221 and the light detector 222 i.e. operations of measuring a parameter relating to a pulse wave of the subject in accordance with a predetermined measurement program. Specifically, the measurement controller 41 issues a timing pulse or a like signal to the emission controlling circuit 31 and to the A/D conversion circuit 32 to control the light emitter 221 to emit light at a predetermined sampling frequency, and controls the light detector 222 to acquire a photoelectric conversion signal i.e. measurement data in synchronism with the emission timing.

The recording controller 42 is operative to record the digital measurement data outputted from the A/D conversion circuit 32 into the memory section 51 in association with measurement time information, using a timer function or a like function equipped in the CPU.

The analysis processing section 43 executes a data analysis with respect to the photoelectric pulse wave data which has been acquired by the probe 22 and temporarily stored in the memory section 51, or directly with respect to the photoelectric pulse wave data acquired by the probe 22 so as to provide a broad-ranging detection on cases. For this purpose, the analysis processing section 43 has plural analysis processors for analyzing the pulse wave to diagnose plural cases. A detailed arrangement on a functional construction of the analysis processing section 43 will be described later in detail, referring to FIG. 4.

The display controller 44 controls the display section 212 to display measurement status information including pilot information indicating that a measurement is being conducted, or an analysis result or the like obtained by the analysis processing section 43 in a predetermined display format. Also, the display controller 44 controls the display section 212 to selectively or simultaneously display the analysis results for plural cases obtained by the analysis processing section 43 depending on a detection condition. Furthermore, the display controller 44 controls the display section 212 to display the analysis result in different display modes, using text, numeral, symbol, pictorial, or character information. Examples of the display manner will be described later, referring to FIGS. 17A through 22.

The display section 212 includes an LCD (Liquid Crystal Display) device, and displays the measurement status information, the analysis result depending on the cases, or like information in the form of an appropriate indication such as text, numeral, symbol, pictorial, or character information.

The memory section 51 may include an ROM, an EEPROM, and an involatile memory such as a flash memory. The memory section 51 stores therein the measurement data acquired by the pulse oximeter 20, as well as the operation program or a like program for the pulse oximeter 20. Specifically, the memory section 51 temporarily stores therein the 2-wavelength photoelectric pulse wave data or the 1-wavelegnth photoelectric pulse wave data outputted from the measurement circuit section 30, or the instantaneous $SpO_2$ values acquired out of the 2-wavelength photoelectric pulse wave data, and, according to needs, data concerning body movements/body positions which are outputted from the acceleration sensor 55 in association with the sampling timing.

The operating section 52 includes operation buttons, and is used to enter designation on measurement start by the main controller 40, or information relating to various operation commands. The I/F section 53 is an interface device for enabling communication of the data recorded in the memory section 51 with another electrical device such as a personal computer in transferring the data to the electrical device. The power source section 54 includes a power source circuit and a power battery such as a button battery, and supplies a drive voltage to the respective elements in the performance part of the pulse oximeter 20.

The acceleration sensor 55 functions as a sensor for detecting a body movement or a body position of the subject. Examples of the acceleration sensor 55 are a piezoresistive 2-axis or 3-axis sensor, a capacitance sensor, and a magnetic sensor. For instance, a piezoresistive 3-axis acceleration sensor has a rectangular frame-like support member, a weight disposed in the middle of the support member, and thin beam portions connecting the weight and the support member in four directions, wherein piezoresistive devices are provided on the beam portions. When an external force is applied to the acceleration sensor, specifically, when a vibration, a tilting force, or a like external force based on a body movement of the subject is applied to the device body 21 of the pulse oximeter 20, the weight is displaced around X-axis, Y-axis, or in Z-axis direction depending on the body movement, thereby deforming the relevant beam portion. As a result, a stress in accordance with the deformation is applied to the piezoelectric device on the beam portion. The application of the stress changes a resistance of the piezoresistive device. Detecting the change in resistance i.e. a signal proportional to the acceleration enables to detect an oscillation of the device body 21, in other words, detect a body movement or a body position of the subject.

Detailed Description on Analysis Processing Section

Figure 4:
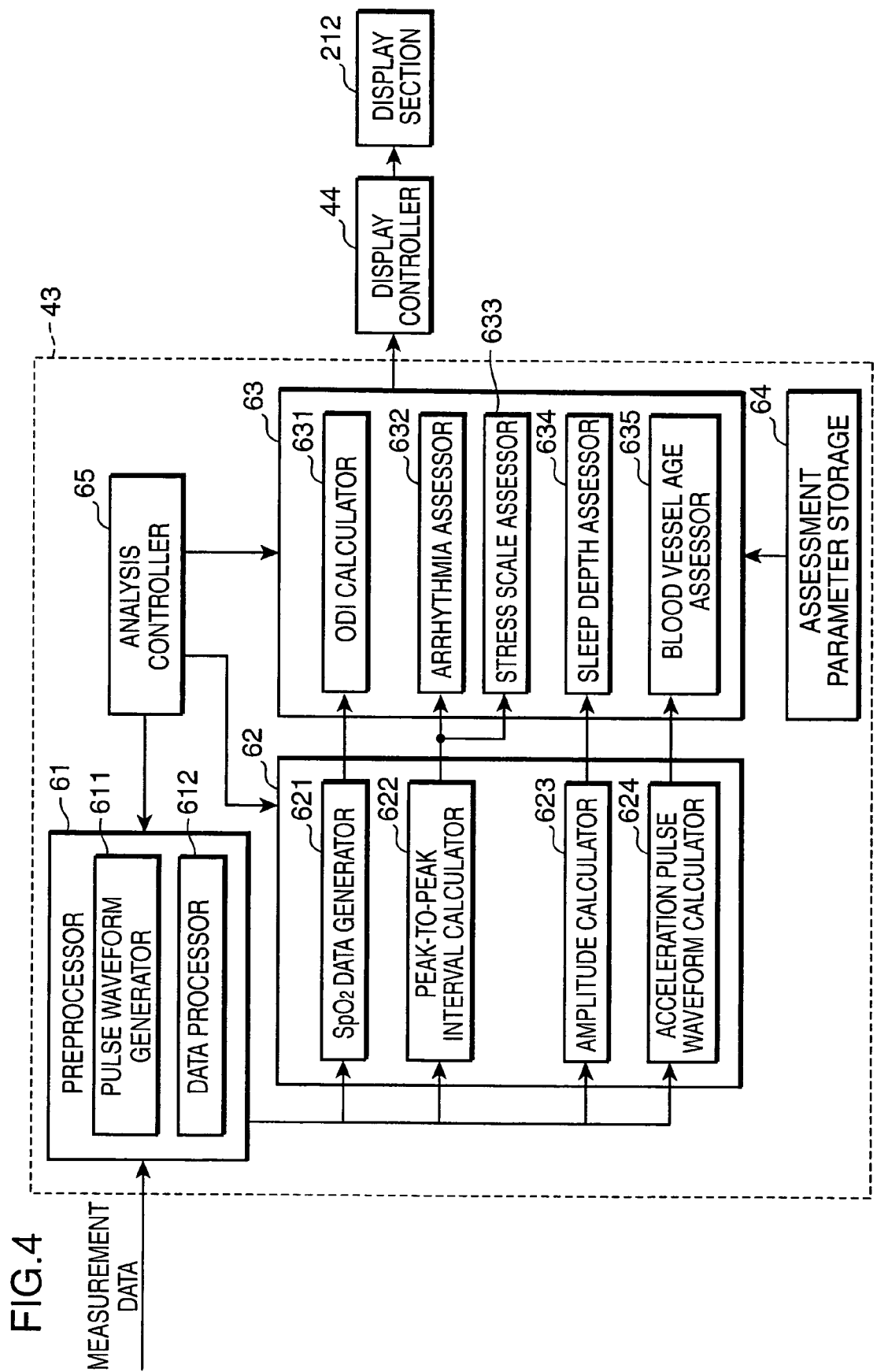
FIG. 4 is a block diagram showing a functional construction of an analysis processing section.

In this section, the arrangement of the analysis processing section 43 is described in detail. FIG. 4 is a block diagram showing an arrangement of a functional construction of the analysis processing section 43. The analysis processing section 43 in this embodiment is provided with a calculating section and an assessing section for performing analyses depending on the following cases.

(1) Using 2-wavelength pulse waveform detecting ODI (Oxygen Desaturation Index), which corresponds to the number of appearances of a peak where the $SpO_2$ value is lowered than a predetermined value per hour, as a sleep apnea index (2) Using 1-wavelength pulse waveform detecting a) arrhythmia, b) degree of stress, c) depth of sleep, and d) blood vessel age In the following, approaches for detecting the above cases are briefly described.

1) ODI

The ODI is obtained by: acquiring an $SpO_2$ curve representing a time-based change in $SpO_2$ value; counting the number of appearances of a peak where the $SpO_2$ value is lowered than a predetermined value e.g. 90%, (hereinafter, called as "Dip", which appears in the case where the subject suffers a respiratory failure); and performing a computation of converting the counted number into the number of appearances of the Dip per hour. The larger the number of appearances of the Dip is, the more likely the subject is diagnosed to be a severe SAS patient. The $SpO_2$ curve is created by: obtaining an instantaneous $SpO_2$ value at each sampling frequency based on a variation in transmitted amounts of the red light of the wavelength $\lambda 1$ and the infrared light of the wavelength $\lambda 2$, i.e. based on light absorption characteristics of hemoglobin, using 2-wavelength photoelectric pulse wave data based on e.g. the red light of the wavelength $\lambda 1$ and the infrared light of the wavelength $\lambda 2$; and developing the instantaneous $SpO_2$ values along a time axis.

(2-a) Arrhythmia

An arrhythmia can be detected based on a degree of variation in a pulse wave interval of a 1-wavelegnth photoelectric pulse waveform e.g. a pulse wave peak-to-peak interval, which is an interval between two consecutive peak values (not necessarily a maximal value) each appearing per heartbeat. Generally, if a trend graph concerning the pulse wave peak-to-peak intervals is created for a normal healthy person, the pulse wave peak-to-peak interval substantially constantly appears within about 1 second despite a slight variation. On the other hand, in the case of an atrial fibrillation patient, the pulse wave peak-to-peak intervals appear at random without regularity resulting from an atrial fibrillation. In the case of an extrasystolic arrhythmia patient, the pulse wave peak-to-peak intervals appear at two local portions e.g. within about 1.2 seconds and within about 1.5 seconds, because a short heartbeat interval and a long heartbeat interval are likely to be alternately and cyclically repeated in the extrasystolic arrhythmia patient. Electrocardiogram RR-intervals obtained by analyzing a measured electrocardiogram using a holter monitor or a like device is widely used as measurement data for diagnosing an arrhythmia, and it is confirmed that the pulse wave peak-to-peak intervals have a high correlation to the electrocardiogram RR-intervals.

(2-b) Degree of Stress

Similarly to the arrhythmia, the degree of stress can be detected based on a degree of variation in a pulse wave peak-to-peak interval. As mentioned above, there is observed a slight variation in pulse wave peak-to-peak intervals of a normal healthy person. However, it is observed that the function of the autonomic nervous system of the normal healthy person is likely to be lowered as a degree of stress is increased, with the result that the variation in pulse wave peak-to-peak intervals substantially disappears. Thus, the degree of stress of the subject can be assessed by discriminating pulse wave peak-to-peak intervals with a slight variation, which appear while the subject is in a normal condition i.e. in a less stressful condition from pulse wave peak-to-peak intervals with no variation, which appear while the subject is in a highly stressful condition based on typical patterns. It is possible to diagnose an autonomic disorder by using an assessment approach similar to the above.

(2-c) Depth of Sleep

The depth of sleep can be assessed by analyzing amplitude values of a 1-wavelength photoelectric pulse waveform. Generally, the amplitude of a pulse waveform is small, and a variation in amplitude is large in light sleep, whereas the amplitude of a pulse waveform is large, and a variation in amplitude is small in deep sleep. In view of this, the depth of sleep can be assessed by analyzing a magnitude of an amplitude of a pulse waveform or a variation in amplitude.

(2-d) Blood Vessel Age

The blood vessel age can be estimated based on an acceleration pulse waveform obtained by a second order derivation of a 1-wavelegnth photoelectric pulse waveform. Specifically, the blood vessel age can be estimated by generating an acceleration pulse waveform and obtaining a characteristic on the acceleration pulse waveform. Characteristics on an acceleration pulse waveform differ among ages i.e. generations, which conceivably results from a change in blood vessel resilience, which is a resilience force of a blood vessel. In view of this, an estimate value of the blood vessel age can be obtained by: preparing typical acceleration pulse waveform patterns depending on generations in advance; and by assessing an analogy between the typical acceleration pulse waveform patterns and the obtained acceleration pulse waveform based on a frequency analysis or a like technique.

As shown in FIG. 4, the analysis processing section 43 is provided with a preprocessor 61, a calculating section 62, an assessing section 63, an assessment parameter storage 64, and an analysis controller 65 to enable the aforementioned case diagnoses.

Figure 5:
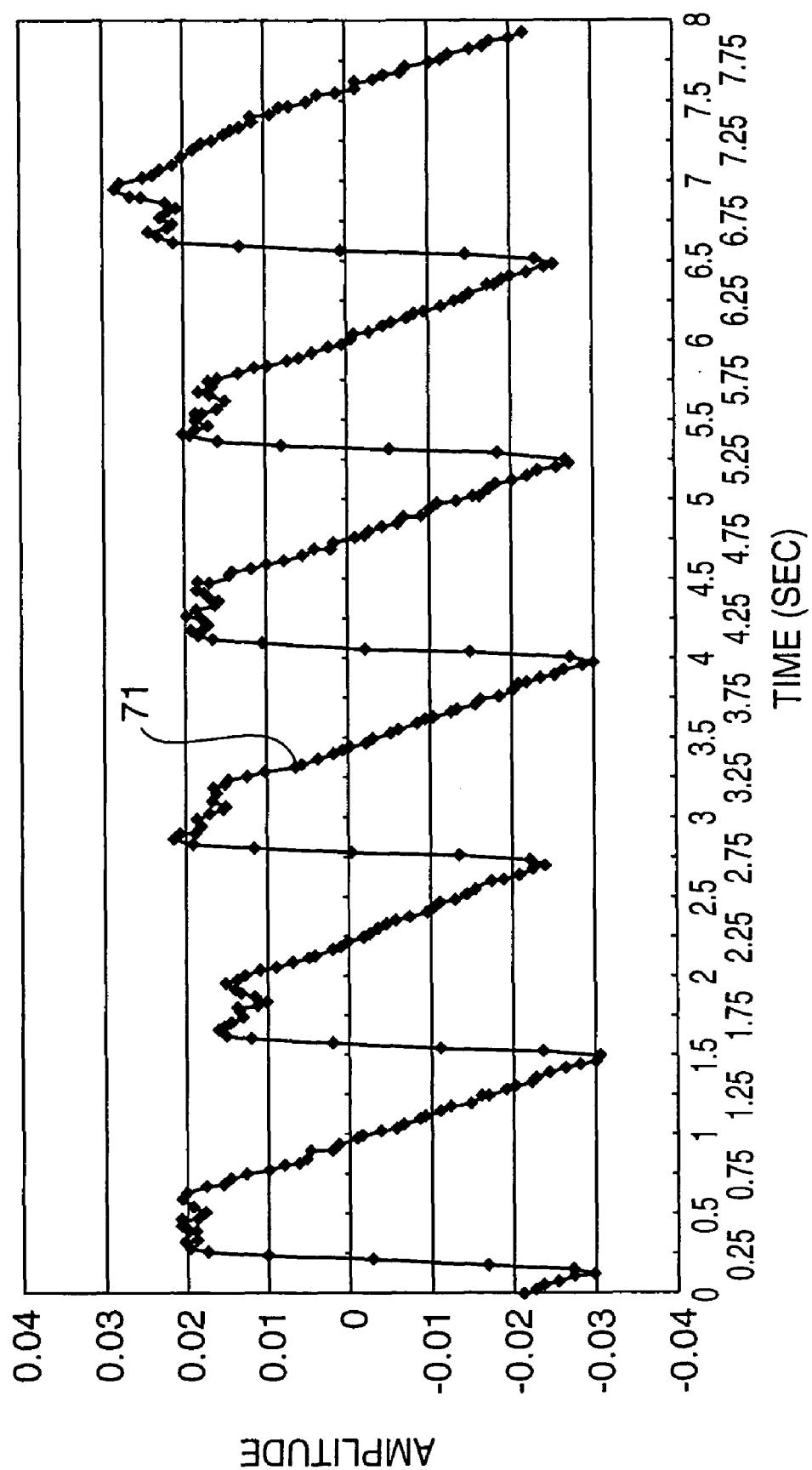
FIG. 5 is a graph showing an example of a photoelectric pulse waveform.

The preprocessor 61 generates a predetermined photoelectric pulse waveform so that the calculating section 62 executes a computation based on a 1-wavelength photoelectric pulse waveform or a 2-wavelegnth photoelectric pulse waveform. The preprocessor 61 has a pulse waveform generator 611 and a data processor 612. The pulse waveform generator 611 reads, out of the memory section 51, the photoelectric pulse wave data that has been acquired at a predetermined sampling frequency and stored in the memory section 51 in association with time information, performs a data alignment process of developing the photoelectric pulse wave data along a time axis, and generates a 1-wavelegnth photoelectric pulse waveform or a 2-wavelength photoelectric pulse waveform. FIG. 5 is a graph showing an example of a photoelectric pulse waveform 71 to be generated by the pulse waveform generator 611, wherein the sampling frequency of the pulse waveform is 30 Hz.

The data processor 612 performs a noise removal process and a moving averaging process with respect to the photoelectric pulse waveform 71. The photoelectric pulse waveform 71 shown in FIG. 5 is a waveform obtained by plotting raw pulse wave data. A variation in pulse waveform within a small measurement duration frequently appears in the photoelectric pulse waveform 71 based on the raw pulse wave data. In view of this, the data processor 612 executes a moving averaging process of obtaining an average with respect to five pulse wave data plotted on a time axis of the photoelectric pulse waveform 71, i.e. with respect to central data, and two consecutive data each preceding and succeeding to the central data, and executes the averaging with respect to the photoelectric pulse waveform 71 sequentially along the time axis.

The data processor 612 also executes a process of eliminating measurement data that has been detected while the subject was in an abnormal body position based on body movement data or body position data detected by the acceleration sensor 55. Specifically, it is required to obtain the ODI based on variations in $SpO_2$ during sleep of the subject. Accordingly, it is necessary to eliminate measurement data that has been acquired while the subject was awakened and made a movement such as walking during the measurement. In this embodiment, the period when the subject was in a seated position, which is highly likely to include walking position, can be specified by analyzing data concerning an axial output from the acceleration sensor 55. Accordingly, the data processor 612 executes a process of handling the measurement data acquired while the subject was in the seated position as abnormal data, and discarding the abnormal data.

The calculating section 62 performs a computation of analyzing data necessary for diagnosing the aforementioned cases i.e. data corresponding to the photoelectric pulse waveform outputted from the preprocessor 61. The calculating section 62 is provided with an $SpO_2$ data generator 621, a peak-to-peak interval calculator 622, an amplitude calculator 623, and an acceleration pulse waveform calculator 624. The $SpO_2$ data generator 621 is provided for assessment of an ODI, the peak-to-peak interval calculator 622 is provided for assessment of an arrhythmia and a degree of stress. The amplitude calculator 623 is provided for assessment of a blood vessel age.

Figure 6:
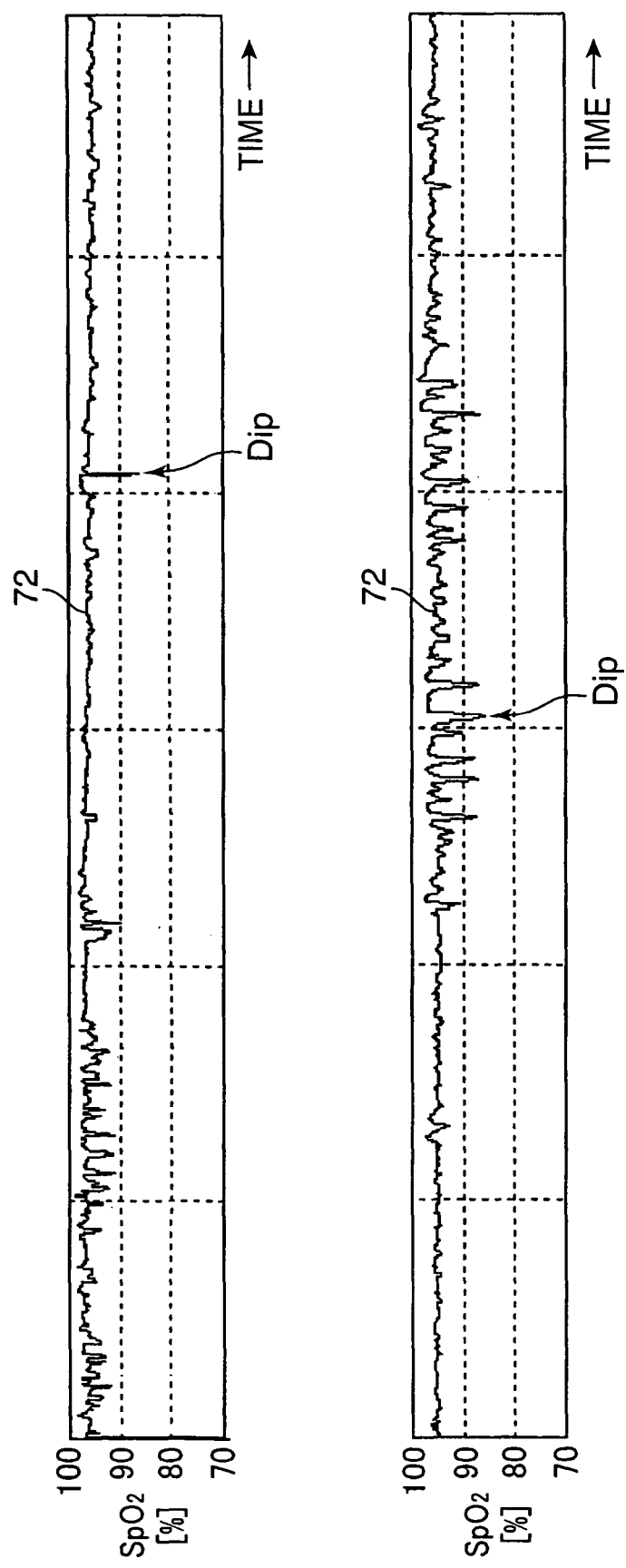
FIG. 6 is a graph showing an example of an $SpO_2$ curve.

The $SpO_2$ data generator 621 generates an $SpO_2$ curve by: obtaining an instantaneous $SpO_2$ value at each sampling frequency based on 2-wavelegnth photoelectric pulse wave data or a 2-wavelength photoelectric pulse waveform based on the red light of the wavelength $\lambda 1$ and the infrared light of the wavelength $\lambda 2$, i.e., pulse wave data processed by the preprocessor 61, or reading the instantaneous $SpO_2$ value at each sampling frequency, which has been predefined based on the 2-wavelength photoelectric pulse wave data, out of the memory section 51; and by developing the instantaneous $SpO_2$ values along a time axis. FIG. 6 is a graph showing an example of an $SpO_2$ curve 72 obtained by the above process, wherein the time axis is divided into an upper section and a lower section. Portions in the $SpO_2$ curve 72 where the $SpO_2$ value is temporarily lowered correspond to the Dip.

Figure 7:
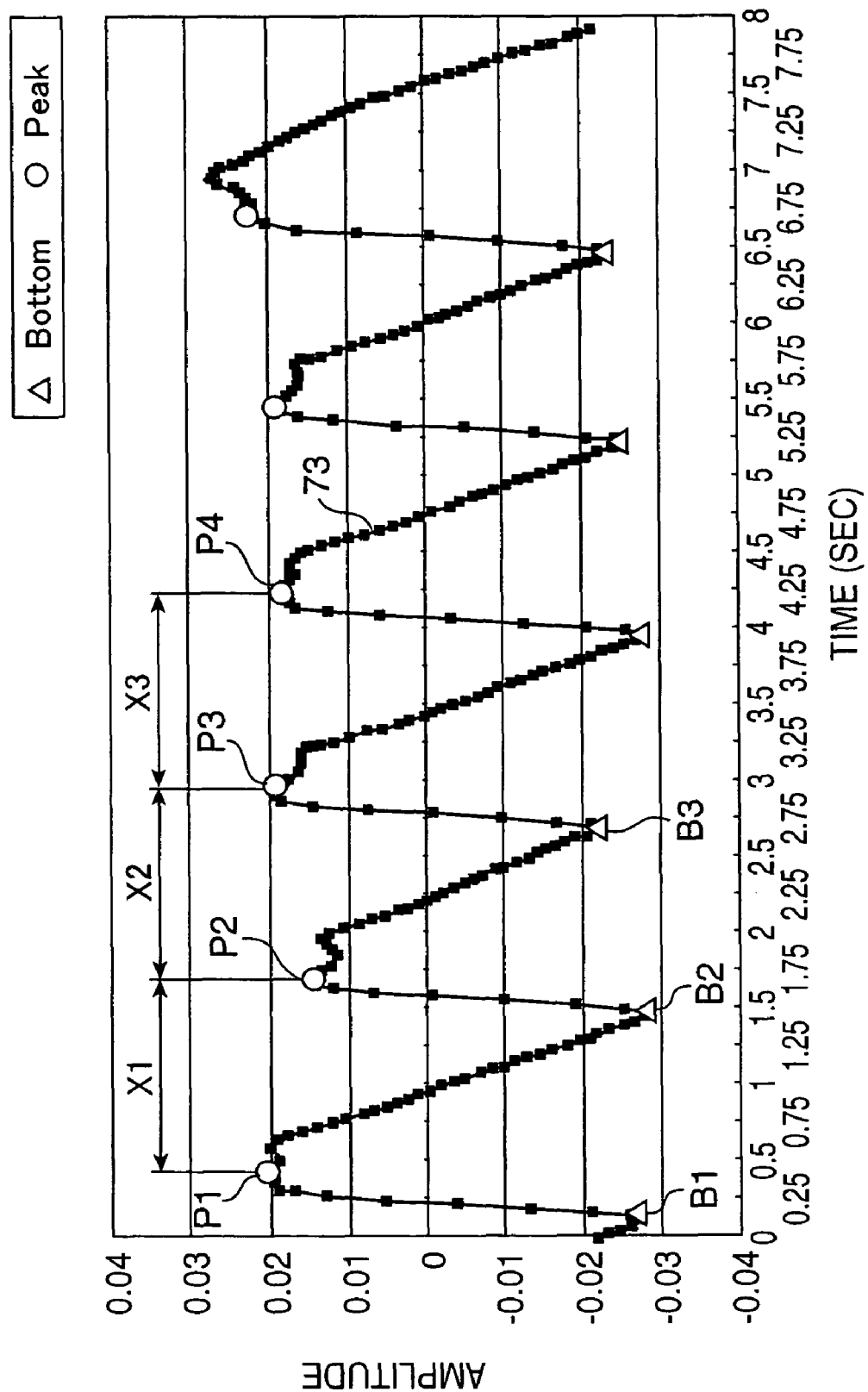
FIG. 7 is a graph explaining an approach of obtaining pulse wave peak-to-peak intervals.

The peak-to-peak interval calculator 622 executes a computation of obtaining intervals each between two consecutive peak values of the photoelectric pulse waveform generated by the preprocessor 61 i.e. pulse wave peak-to-peak intervals. FIG. 7 is a graph for describing an approach of obtaining the pulse wave peak-to-peak intervals. The waveform shown in FIG. 7 is a photoelectric pulse waveform 73 obtained by executing a moving averaging process with respect to the photoelectric pulse waveform 71. Pulse wave peak-to-peak intervals of the photoelectric pulse waveform 73 are obtained by: specifying peak values P1, P2, P3, P4, ... each appearing per heartbeat; and sequentially obtaining intervals between the peak values P1 and P2, P2 and P3, P3 and P4 .... Alternatively, pulse wave bottom-to-bottom intervals may be obtained by: specifying bottom values B1, B2, B3, B4, ... each appearing per heartbeat; and sequentially obtaining intervals between the bottom values B1 and B2, B2 and B3, B3 and B4, .... In specifying the peak values P1, P2, P3, P4, ..., it is desirable to perform a process of removing notch noises included in the waveform by utilizing amplitude value data concerning differences between bottom values and peak values, or the like.

The amplitude calculator 623 performs a process of making pairs each with a bottom value and a peak value appearing per heartbeat with respect to the photoelectric pulse waveform generated by the preprocessor 61, and obtaining bottom-to-peak amplitude values each being a difference between the bottom value and the peak value in each of the pairs along the time axis. Specifically, the amplitude calculator 623 performs a computation of obtaining bottom-to-peak amplitude values each with respect to a bottom value and a peak value adjacent to each other along the time axis, such as a difference between the bottom value B1 and the peak value P1, a difference between the bottom value B2 and the peak value P2, and so on. The bottom-to-peak amplitude values are developed along the time axis, and are used as data to be assessed by a sleep depth assessor 634 to be described later.

Figure 8:
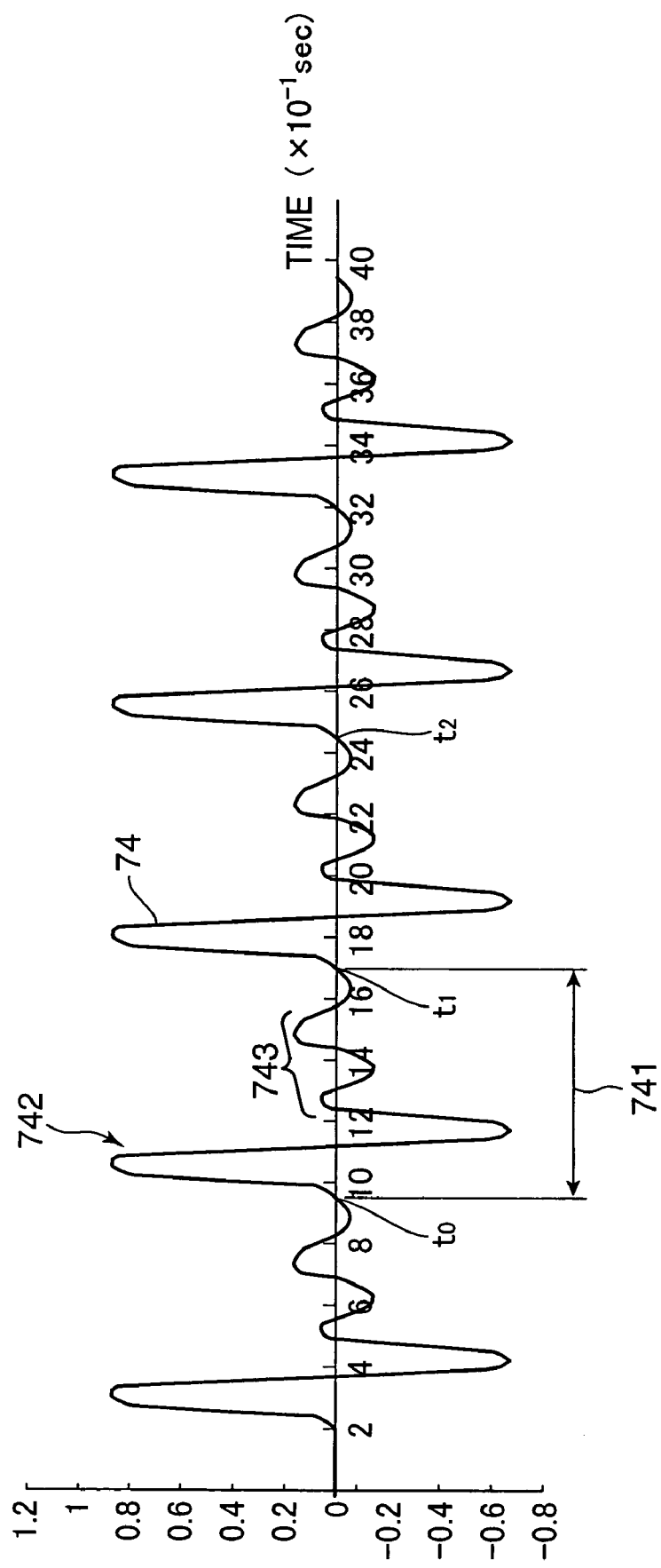
FIG. 8 is a graph showing an example of an acceleration pulse waveform obtained by a second-order derivation of a photoelectric pulse waveform.

The acceleration pulse wave calculator 624 performs a computation of obtaining an acceleration pulse wave by a second order derivation of the photoelectric pulse waveform generated by the preprocessor 61. FIG. 8 is a graph showing an example of an acceleration pulse waveform 74 obtained by a second order derivation of the photoelectric pulse waveform 73 shown in FIG. 7. In the acceleration pulse waveform 74, a pulse wave component in a time zone indicated by the reference numeral 741 corresponds to a pulse wave component within one heartbeat. The pulse wave component within the one heartbeat includes a large variation in waveform indicated by the reference numeral 742, followed by a group of small variations in waveform indicated by the reference numeral 743. The pulse wave component having the above pattern is cyclically repeated to constitute the acceleration pulse waveform 74. The characteristic of the acceleration pulse waveform 74, specifically, the group of small waveform variations indicated by the reference numeral 743 is an item to be assessed by a blood vessel age assessor 635 to be described later.

The assessing section 63 performs an assessment depending on the cases based on the processed data of the photoelectric pulse waveform obtained in the respective parts of the calculating section 62. The assessing section 63 is provided with an ODI calculator 631, an arrhythmia assessor 632, a stress scale assessor 633, the sleep depth assessor 634, and the blood vessel age assessor 635.

Figure 9:
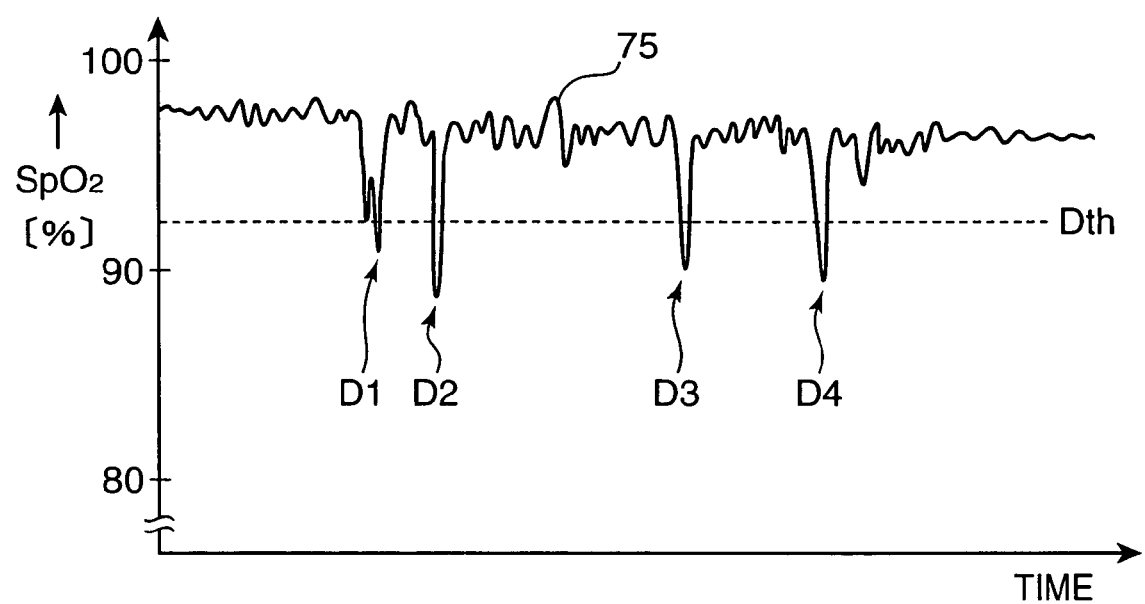
FIG. 9 is a graph schematically showing a process to be executed by an ODI calculator.

The ODI calculator 631 obtains a sleep apnea index by: counting the number of appearances of Dip based on the $SpO_2$ curve generated by the $SpO_2$ data generator 621; and performing a computation of converting the counted number into the number of appearances of Dip per hour. FIG. 9 is a graph schematically showing a process to be executed by the ODI calculator 631. In FIG. 9, a threshold value Dth is set to 92%, and a peak where the $SpO_2$ value is lowered than the threshold value Dth is defined as Dip. In the example of FIG. 9, the Dip is observed four times, in other words D1 through D4 are observed as the Dip. The ODI calculator 631 counts the number of appearances of the Dip per hour, and outputs the counted number as a sleep apnea index.

Figure 10A:
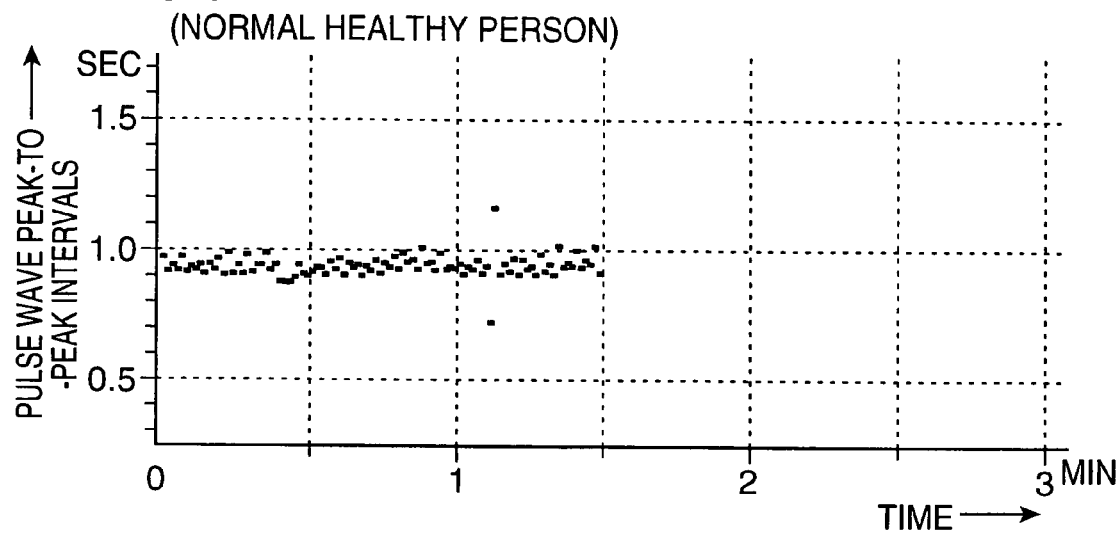
Figure 10B:
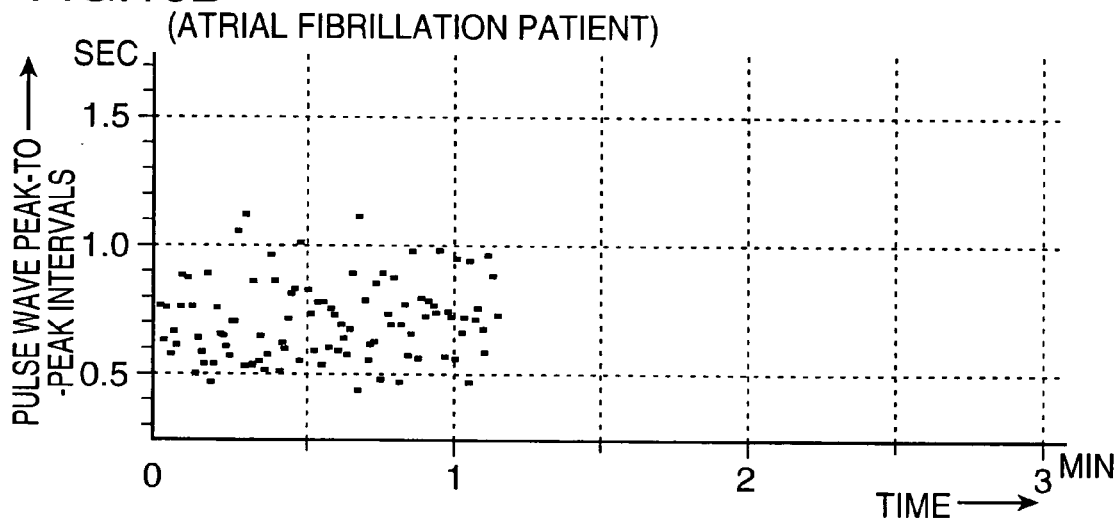
Figure 10C:
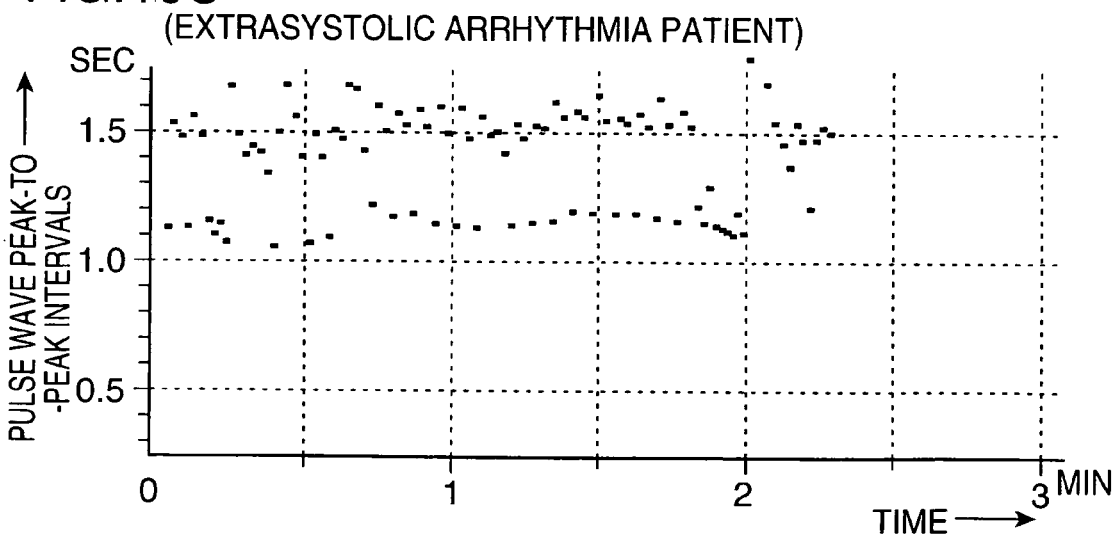

The arrhythmia assessor 632 creates a trend graph concerning pulse wave peak-to-peak intervals by developing the pulse wave peak-to-peak intervals obtained by the peak-to-peak calculator 622 along a time axis. With use of the trend graph, cases on an arrhythmia can be found. FIGS. 10A through 10C are trend graphs concerning the pulse wave peak-to-peak intervals, showing examples of diagnosing an arrhythmia. FIG. 10A is a trend graph obtained from a normal healthy person, wherein the pulse wave peak-to-peak intervals primarily appear within about 1 second despite a slight variation. FIG. 10B is a trend graph obtained from an atrial fibrillation patient, wherein the pulse wave peak-to-peak intervals appear at random without regularity resulting from an atrial fibrillation. FIG. 10C is a trend graph obtained from an extrasystolic arrhythmia patient, wherein the pulse wave peak-to-peak intervals appear at two local portions i.e. within about 1.2 seconds and within about 1.5 seconds. The arrhythmia assessor 632 may perform a computation of adding an arrhythmia period when one of the symptoms as shown in FIGS. 10A, 10B, and 10C is observed.

Figure 11:
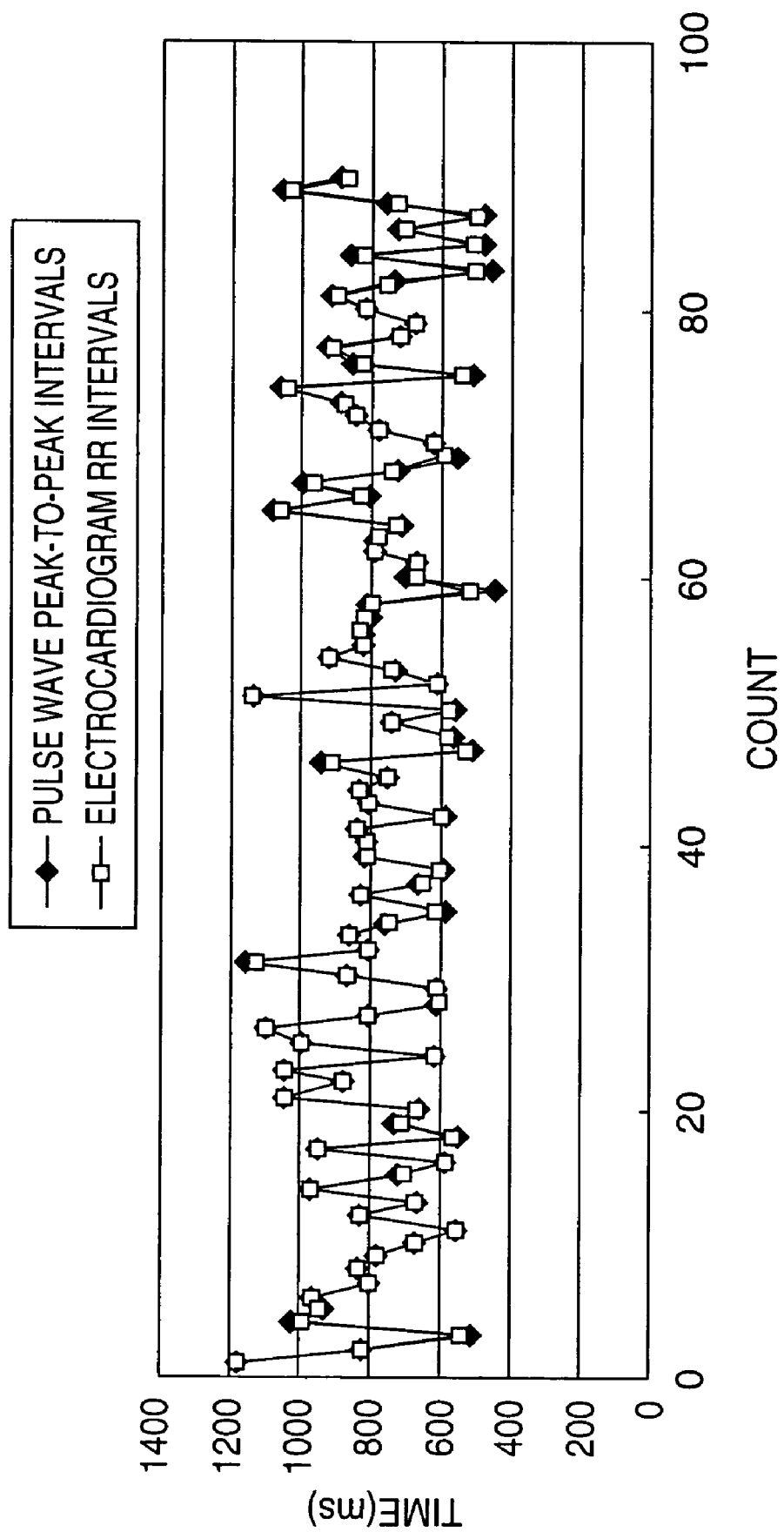
FIG. 11 is a graph displaying electrocardiogram RR-intervals and pulse wave peak-to-peak intervals on a common time axis.

FIG. 11 is a graph obtained by: removably attaching a holter monitor and a photoelectric pulse wave sensor onto a subject; concurrently measuring an electrocardiogram and a pulse waveform for a certain period; obtaining electrocardiogram RR-intervals and pulse wave peak-to-peak intervals based on the electrocardiogram and the pulse waveform; and displaying the electrocardiogram RR-intervals and the pulse wave peak-to-peak intervals along a common time axis. As is obvious from FIG. 11, the electrocardiogram RR-intervals, and the pulse wave peak-to-peak intervals obtained based on the photoelectric pulse waveform have a high correlation to each other. Specifically, the holter monitor and the photoelectric pulse wave sensor have substantially the equivalent detection performance. However, in use of the holter monitor, about five electrodes are required to be attached to the subject's body to detect a cardiac activity potential of the subject, which is stressful to the subject. On the contrary, the photoelectric pulse wave sensor, specifically, the pulse oximeter 20 in the embodiment is advantageous in remarkably reducing stress in wearing because the subject is only required to securely hold his or her fingertip with the probe 22.

Figure 12:
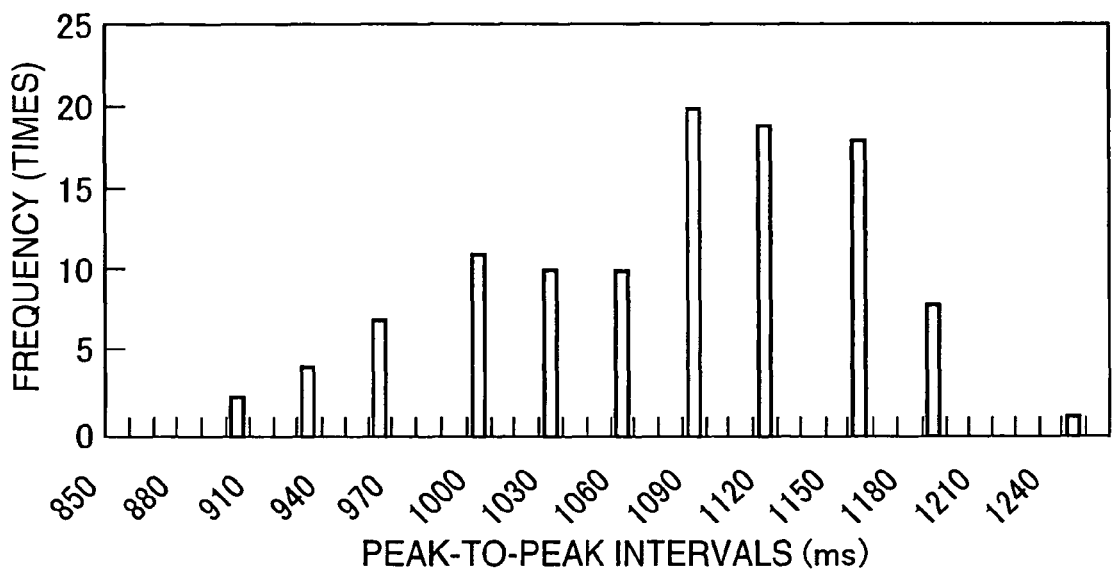

The stress scale assessor 633 creates a histogram relating to the pulse wave peak-to-peak intervals obtained by the peak-to-peak interval calculator 622, and performs a process of assessing a degree of variation in the pulse wave peak-to-peak intervals. FIGS. 12A and 12B are histograms relating to the pulse wave peak-to-peak intervals. FIG. 12A is a histogram typically observed when a normal healthy person is in a normal condition i.e. in a less stressful condition, and FIG. 12B is a histogram typically observed when the normal healthy person is in a highly stressful condition. FIGS. 12A and 12B show that a slight variation is observed with respect to the pulse wave peak-to-peak intervals while the normal healthy person is in a normal condition, and that the function of the autonomic nervous system of the normal healthy person is likely to be lowered as a degree of stress is increased, with the result that the variation in pulse wave peak-to-peak intervals substantially disappears.

Utilizing the above finding, the stress scale assessor 633 obtains an assessment score concerning a degree of stress by: using a stress assessment table in which degrees of variation in pulse wave peak-to-peak intervals, and degrees of stress are correlated to each other; and applying the obtained degree of variation in pulse wave peak-to-peak intervals to the stress assessment table. The stress assessment table is stored in the assessment parameter storage 64.

Figure 13:
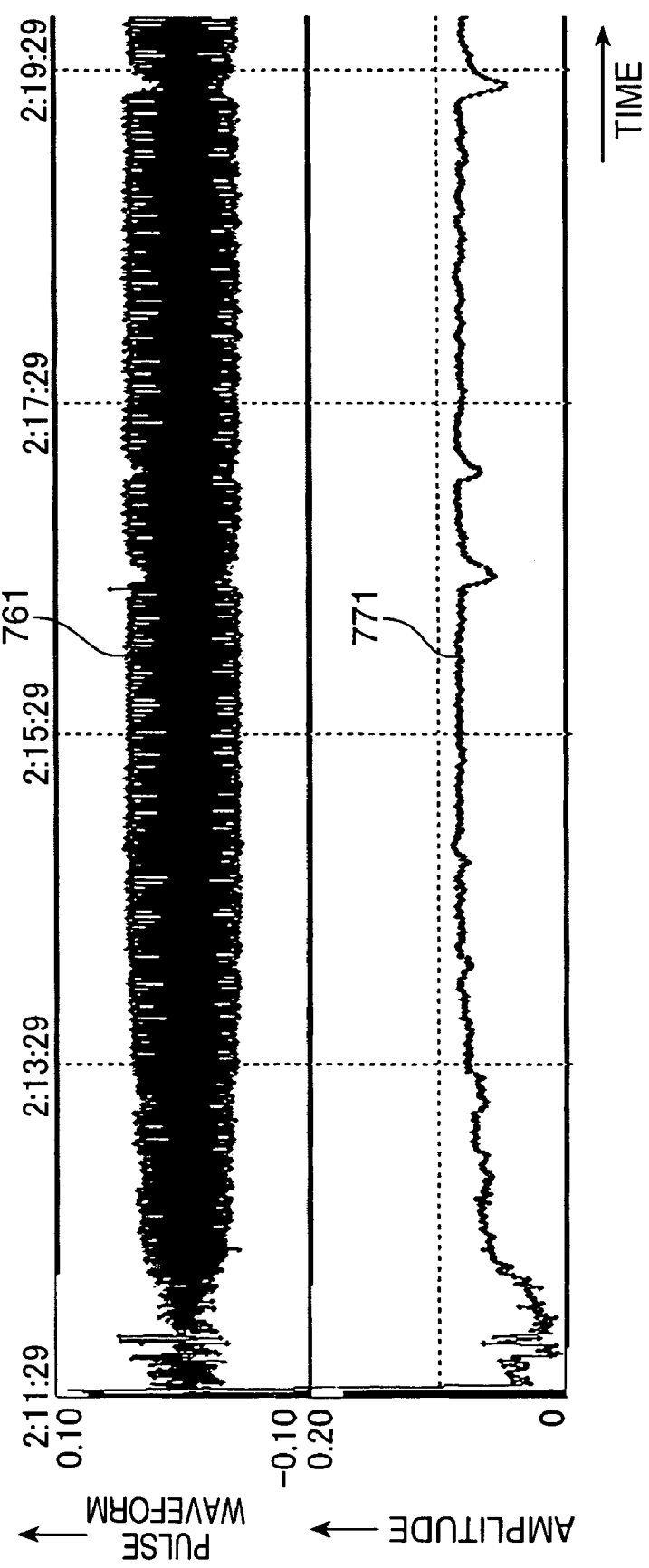
FIG. 13 is a graph obtained by plotting a pulse waveform in an upper section, and bottom-to-peak amplitude values in a lower section on a common time axis.
Figure 14:
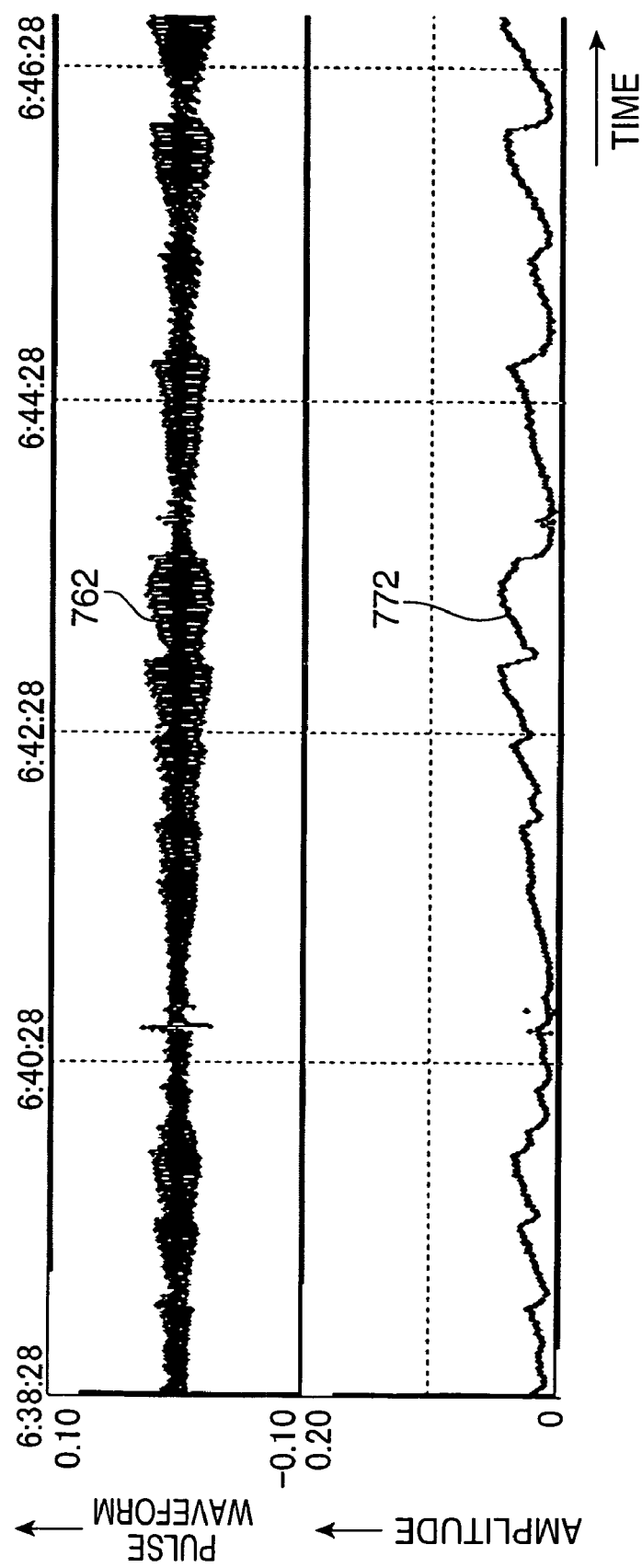
FIG. 14 is a graph obtained by plotting a pulse waveform in an upper section, and bottom-to-peak amplitude values in a lower section on a common time axis.

The sleep depth assessor 634 performs a process of assessing a time-based change in bottom-to-peak amplitude values obtained by the amplitude calculator 623, and obtaining an assessment score concerning a sleep depth. FIGS. 13 and 14 are graphs obtained by concurrently plotting a pulse waveform in the upper section, and bottom-to-peak amplitude values in the lower section obtained by the amplitude calculator 623, along a common time axis. FIG. 13 is a graph showing a pulse waveform 761 and corresponding bottom-to-peak amplitude values 771 in a deep sleep condition. FIG. 14 is a graph showing a pulse waveform 762 and corresponding bottom-to-peak amplitude values 772 in a light sleep condition immediately before awakening.

As is obvious from FIGS. 13 and 14, the deeper the sleep is, the larger the bottom-to-peak amplitude value is, and the smaller the variation in amplitude is; and contrary to this, the lighter the sleep is, the smaller the bottom-to-peak amplitude value is, and the larger the variation in amplitude is. Utilizing the above finding, the sleep depth assessor 634 obtains an assessment score concerning a sleep depth by: using a sleep condition assessment table as shown in FIG. 15, for instance, in which bottom-to-peak amplitude values and sleep conditions are correlated to each other; and applying an average of the bottom-to-peak amplitude values to the sleep condition assessment table. Referring to FIG. 15, REM sleep is a lightest sleep condition, and as the stage is progressed from Stage 1 to Stage 4, the sleep is deepened. Alternatively, a sleep condition assessment table may be prepared by adding a condition which reflects variations of bottom-to-peak amplitude values 771, 772. The sleep condition assessment table is stored in the assessment parameter storage 64.

The blood vessel age assessor 635 obtains an estimate value of a blood vessel age by: comparing the acceleration pulse waveform 74 (see FIG. 8) obtained by the acceleration pulse wave calculator 624 with typical acceleration pulse waveform patterns prepared in correspondence to the generations; and assessing an analogy between the obtained acceleration pulse waveform 74 and the prepared patterns. It is known that the acceleration pulse waveform 74 is varied or differs depending on the ages i.e. generations. FIG. 16 is a graph showing typical acceleration pulse waveform patterns based on the generations with respect to the pulse waveform component per heartbeat indicated by the reference numeral 741 in FIG. 8. As is obvious from FIG. 16, different characteristics are observed among twenties, thirties, forties, and fifties concerning the group of small variations in waveform indicated by the reference numeral 743, following the large variation in waveform indicated by the reference numeral 742. Conceivably, aging results in hardening of the arteries and lowering of a blood vessel resilience, with the result that a response to the pulse wave component indicated by the reference numeral 742 is delayed, thus causing the differences in the waveform component indicated by the reference numeral 743.

Utilizing the above finding, the blood vessel age assessor 635 obtains an assessment score concerning a blood vessel age by comparing the obtained acceleration pulse waveform with the typical acceleration pulse waveform patterns based on the generations. In this embodiment, the assessment parameter storage 64 may store generation-based prototype data corresponding to the typical acceleration pulse waveform patterns as shown in FIG. 16, for instance, and perform a computation of obtaining an analogy between the obtained acceleration pulse waveform and the generation-based prototype data.

The assessment parameter storage 64 stores therein the data to be compared, which is necessary in performing the assessments by the respective parts of the assessing section 63, as mentioned above. The assessment parameter storage 64 stores therein, for instance, the stress assessment table to be used in the process by the stress scale assessor 633, the sleep condition assessment table to be used in the process by the sleep depth assessor 634, and the generation-based prototype data to be used in the process by the blood vessel age assessor 635.

The analysis controller 65 controls the preprocessor 61, the calculating section 62, and the assessing section 63 of the analysis processing section 63 to execute the respective operations in accordance with an operation command signal issued from the operating section 52, and outputs data concerning a predetermined assessment result to the display controller 44. The display controller 44 controls the display section 212 to display an assessment result obtained by the assessing section 63, or interim data obtained in the course of outputting the assessment result, or an appropriate assessment index which reflects the assessment result.

The analysis results concerning the respective cases obtained by the aforementioned approach are displayed on the display section 212 by way of the display controller 44 in an appropriate display format. FIGS. 17A through 17D are plan views showing examples of various display modes to be simultaneously displayed on the display section 212, wherein analysis results by the respective analysis processors provided in the calculating section 62 and in the assessing section 63 in correspondence to the cases are displayed.

Referring to FIGS. 17A through 17D, sleep apnea index, sleep depth, arrhythmia, degree of stress, and blood vessel age as assessment parameters are displayed in this order from the upper section on the screen of the display section 212. On a first display 81 in FIG. 17A, the ODI value itself obtained by the ODI calculator 631 is displayed as an analysis result concerning the sleep apnea index. An index "GOOD" is displayed as an analysis result concerning the sleep depth. The indexes on the sleep depth can be determined based on a degree of appearance of sleep stages as shown in FIG. 15. For instance, if a change in sleep stage is normal, an index "GOOD" is displayed. If an appearance period of Stage 3 or Stage 4 is short, an index "NEED CARE" is displayed. If an appearance period of Stage 1 or Stage 2 or REM sleep is long, an index "POOR" is displayed. Concerning the arrhythmia, an arrhythmia rate is displayed in terms of numeric data. Concerning the degree of stress, an index "GOOD" is displayed. The indexes on the degree of stress may be categorized into "GOOD", "NEED CARE", "POOR", and the like depending on a degree of variation in pulse wave peak-to-peak intervals of histograms shown in FIGS. 12A and 12B, and an index representing the category to which the analysis result belongs may be displayed. The age in terms of generations is displayed as the blood vessel age.

Figure 17A:
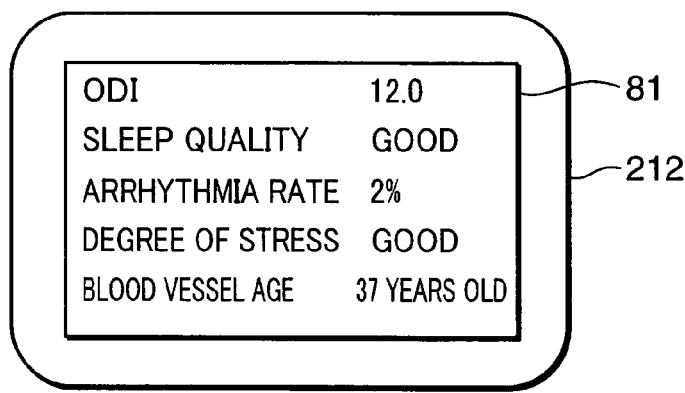
FIGS. 17A through 17D are plan views showing examples of various display modes in which analysis results are displayed simultaneously on a display section.
Figure 17B:
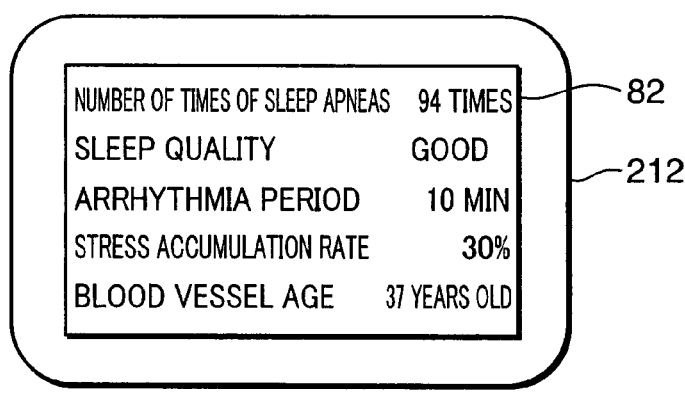

A second display 82 in FIG. 17B is an altered arrangement of the first display 81 to display the analysis result in a more user-friendly manner. Specifically, the number of times of sleep apneas is displayed as the sleep apnea index. Concerning the arrhythmia, the arrhythmia period is displayed in place of the arrhythmia rate in percentage. The degree of stress is displayed in terms of an index "STRESS ACCUMULATION RATE".

Figure 17C:
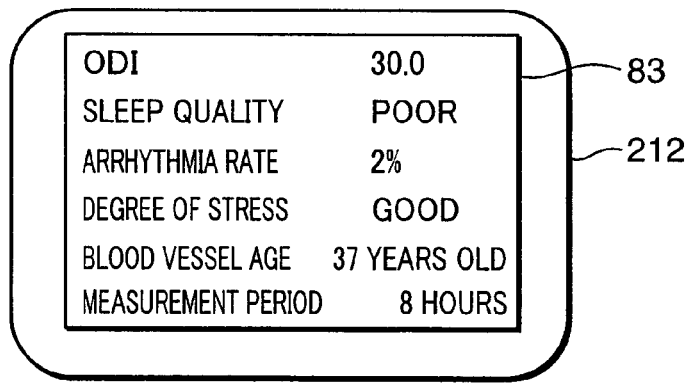

A third display 83 shown in FIG. 17C is an example, in which an indication of displaying a measurement period is additionally provided on a lowermost column. On the third display 83, an assessment index "POOR" is displayed concerning the sleep quality. The item on which an undesirable analysis result is outputted may be displayed in a color e.g. in red.

Figure 17D:
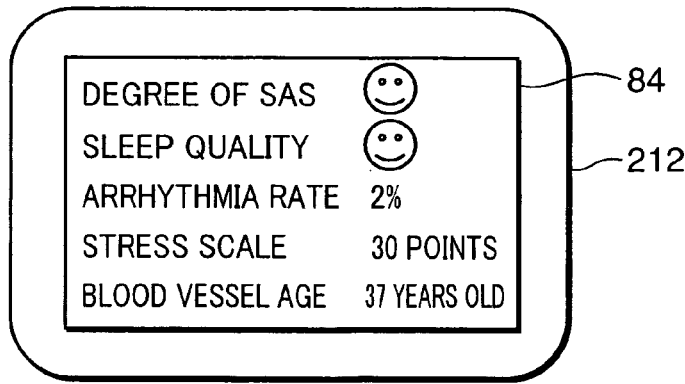

A fourth display 84 shown in FIG. 17D is an example, in which the sleep apnea index and the sleep quality are displayed as pictograms, and the degree of stress is displayed in scores. The display manner makes the display more familiar to users including subjects, other than medical staffs.

The first through the fourth displays 81 through 84 are examples of simplified display images, as a second display mode, of displaying all the assessment results in a simplified manner. The display controller 44 is operable to control the display section 212 to switch over the display mode to a detailed display image, as a first display mode, of displaying an analysis result concerning one case in details as text information, a chart, pictorial information, or a like indication. FIGS. 18 through 22 show examples of the detailed display images. The simplified display image can be switched over to the detailed display image in response to an input of an operation signal from the operating section 52. Alternatively, in the case where the display section 212 has a touch panel function, the switchover may be performed in response to the user's touching one of the display items shown in FIGS. 17A through 17D.

Figure 18:
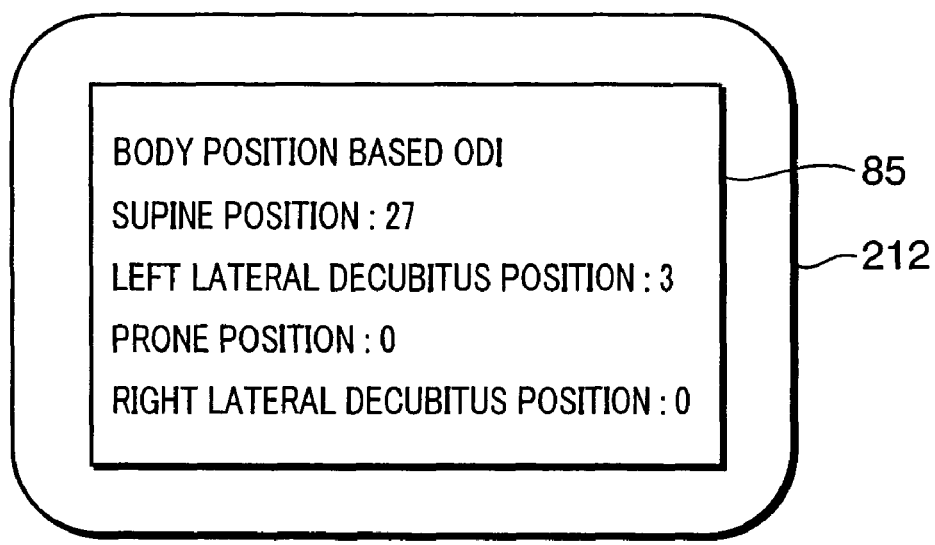
FIG. 18 is a plan view showing an example of displaying an analysis result on an ODI in details.

FIG. 18 is a plan view showing a fifth display 85, which is an example of the detailed display image to be displayed in the case where a detailed display of the ODI is selected. In this example, ODI values based on body positions are displayed. There is a certain correlation between body position and frequency of sleep apneas during sleep among individuals. Accordingly, grasping a condition as to what degree of sleep apnea is caused under what body position allows for providing preventive measures, during sleep, concerning a body position that enables to suppress sleep apneas as much as possible. Therefore, the correlation data is useful analysis information. The body position during sleep can be obtained by analyzing an axial output from the acceleration sensor 55 (see FIG. 3). Thus, body-position-based ODI values can be obtained by adding body position information obtained based on the output voltage from the acceleration sensor 55 in performing a computation by the ODI calculator 631. Also, a time zone of sleep apneas may be additionally displayed. Further alternatively, ODI values in different grades obtained by shifting the threshold value Dth shown in FIG. 9 may be displayed in the form of a list.

Figure 19:
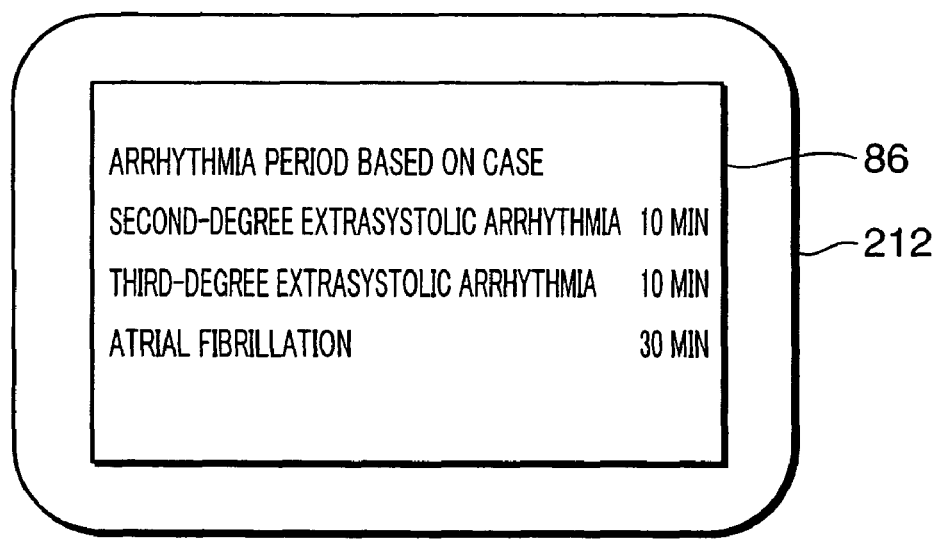
FIG. 19 is a plan view showing an example of displaying an analysis result on an arrhythmia in details.

FIG. 19 is a plan view showing a sixth display 86, which is an example of the detailed display image in the case where a detailed display of arrhythmia is selected. FIG. 19 shows an example of displaying arrhythmia periods corresponding to different kinds of arrhythmia i.e. second-degree extrasystolic arrhythmia, third-degree extrasystolic arrhythmia, and atrial fibrillation. Alternatively, arrhythmia rates based on kinds of arrhythmia, or the numbers of times of arrhythmia based on kinds of arrhythmia may be additionally displayed.

Figure 20:
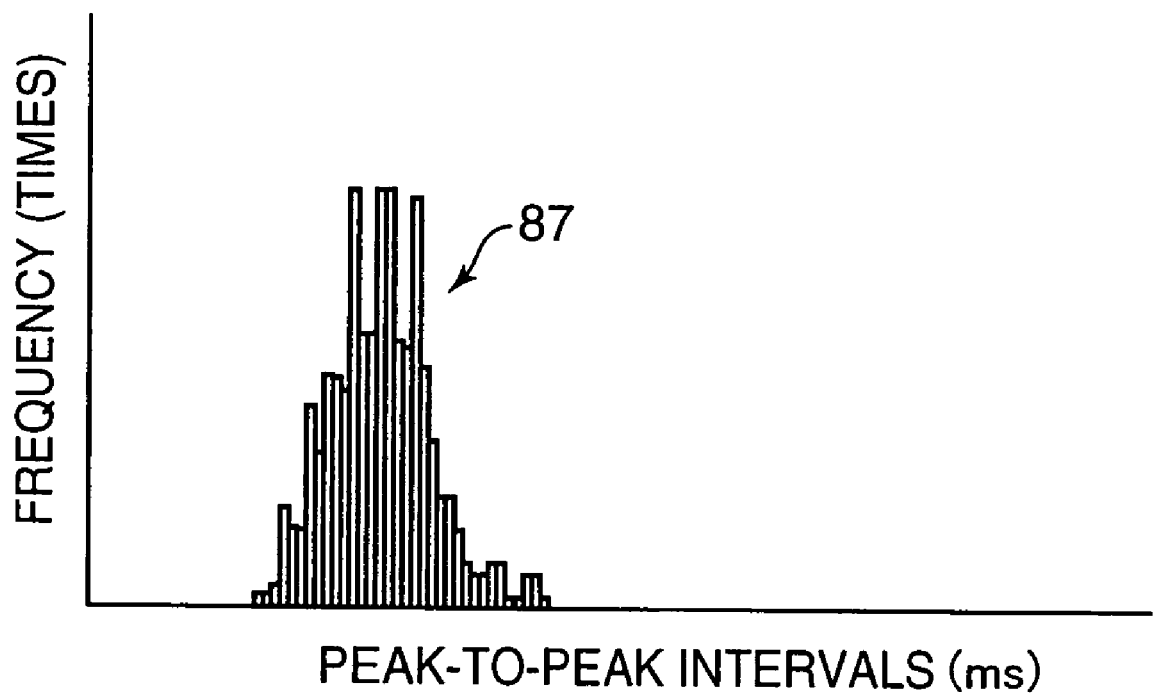
FIG. 20 is a diagram showing an example of displaying an analysis result on a degree of stress as a pictorial indication.

FIG. 20 is a diagram showing a histogram 87 concerning pulse wave peak-to-peak intervals, which is an example of a pictorial indication in the case where a detailed display of a degree of stress is selected. Displaying a pictorial indication in place of text or numeral information enables to enhance visual recognition.

Figure 21A:
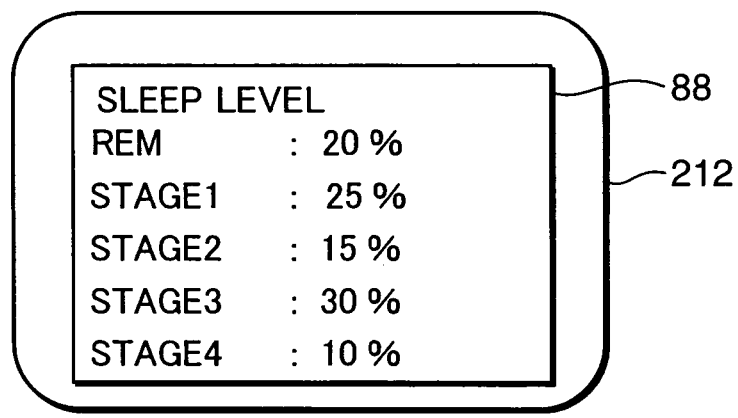
FIG. 21A is a plan view showing an example of displaying an analysis result on sleep depth in details.
Figure 21B:
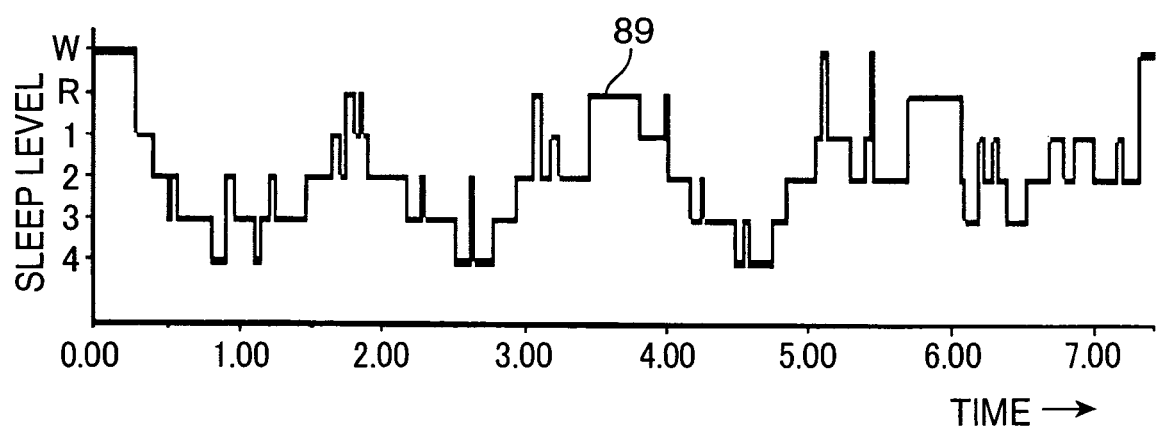
FIG. 21B is a plan view showing an example of displaying the analysis result in FIG. 21A as a pictorial indication.

FIG. 21A is a plan view showing a seventh display 88, which is an example of the detailed display image in the case where a detailed display of a depth of sleep is selected. FIG. 21A shows an example of displaying a degree of appearance of sleep levels shown in FIG. 15 stage by stage in terms of percentage. FIG. 21B is a diagram showing a sleep stage transition graph 89 which is obtained by developing the sleep levels along a time axis. Displaying the sleep stage transition graph 89 on the display section 212 enables to clearly grasp a REM sleep cycle or the like.

Figure 22:
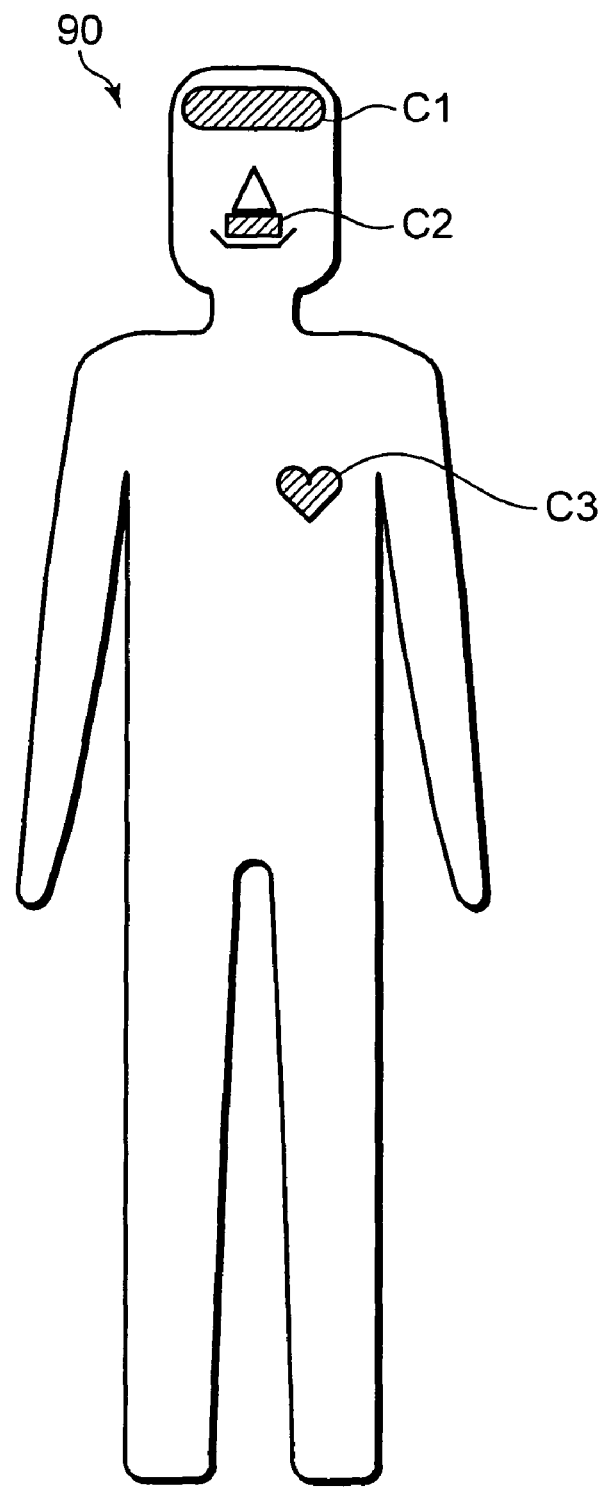
FIG. 22 is a plan view showing an example of superimposedly displaying information relating to analysis results on plural cases over character information.

FIG. 22 is a diagram showing an example of superimposedly displaying information relating to analysis results concerning plural cases over a character image 90 mimicking a human body on the display section 212. For instance, a warning message in red color may be displayed on a portion of the character image 90 where an undesirable analysis result is obtained among the plural analysis results. Specifically, in the case where an undesirable analysis result is obtained concerning a degree of stress, a mark C1 may be superimposedly displayed on the head of the character image 90. In the case where a SAS is observed, a mark C2 may be superimposedly displayed near the mouth of the character image 90. In the case where an arrhythmia is detected, a heart mark C3 may be superimposedly displayed near the heart of the character image 90.

Description on Operation Flow

Figure 23:
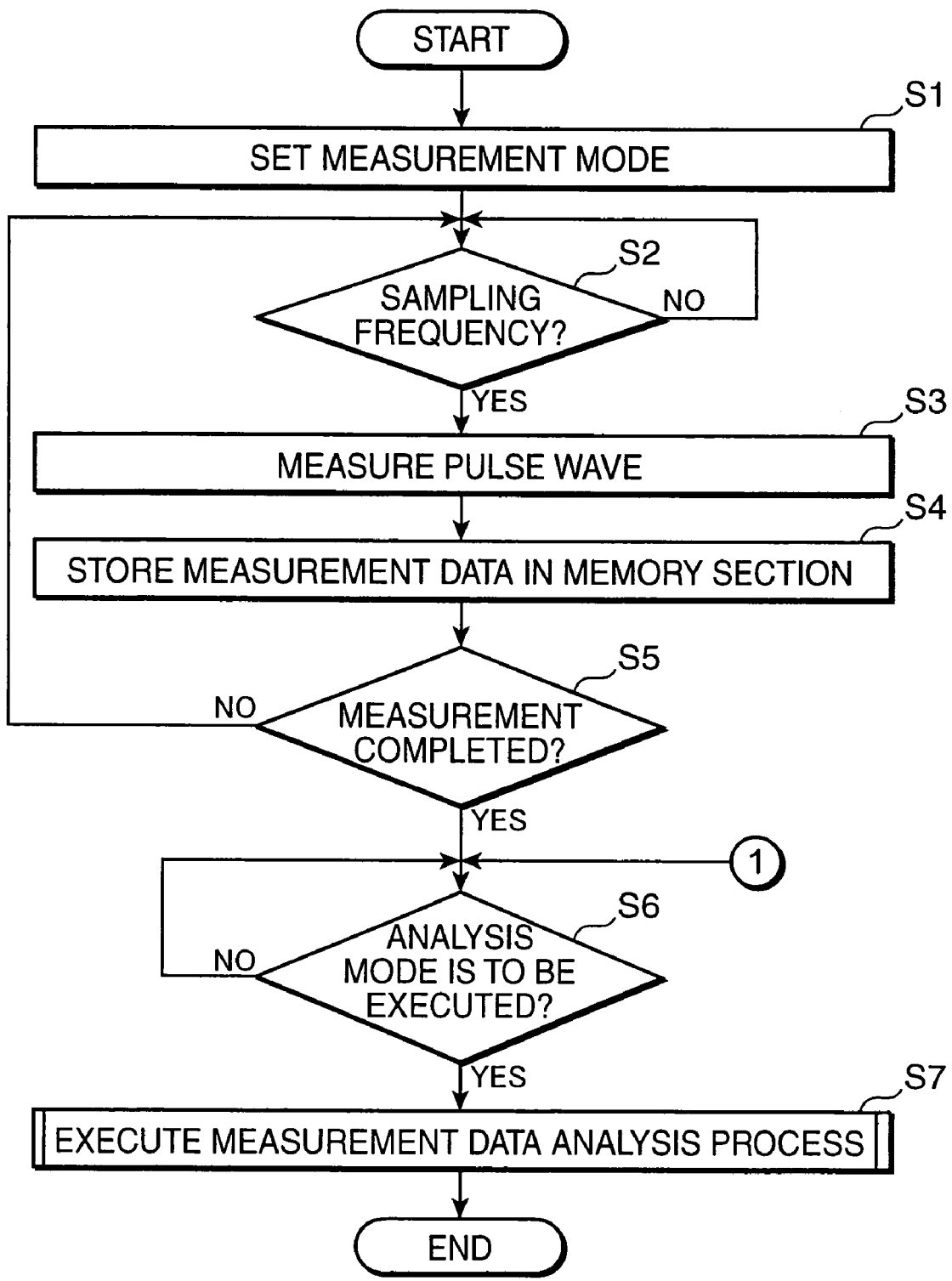
FIG. 23 is a flowchart showing an overall operation flow of the pulse oximeter.
Figure 24:
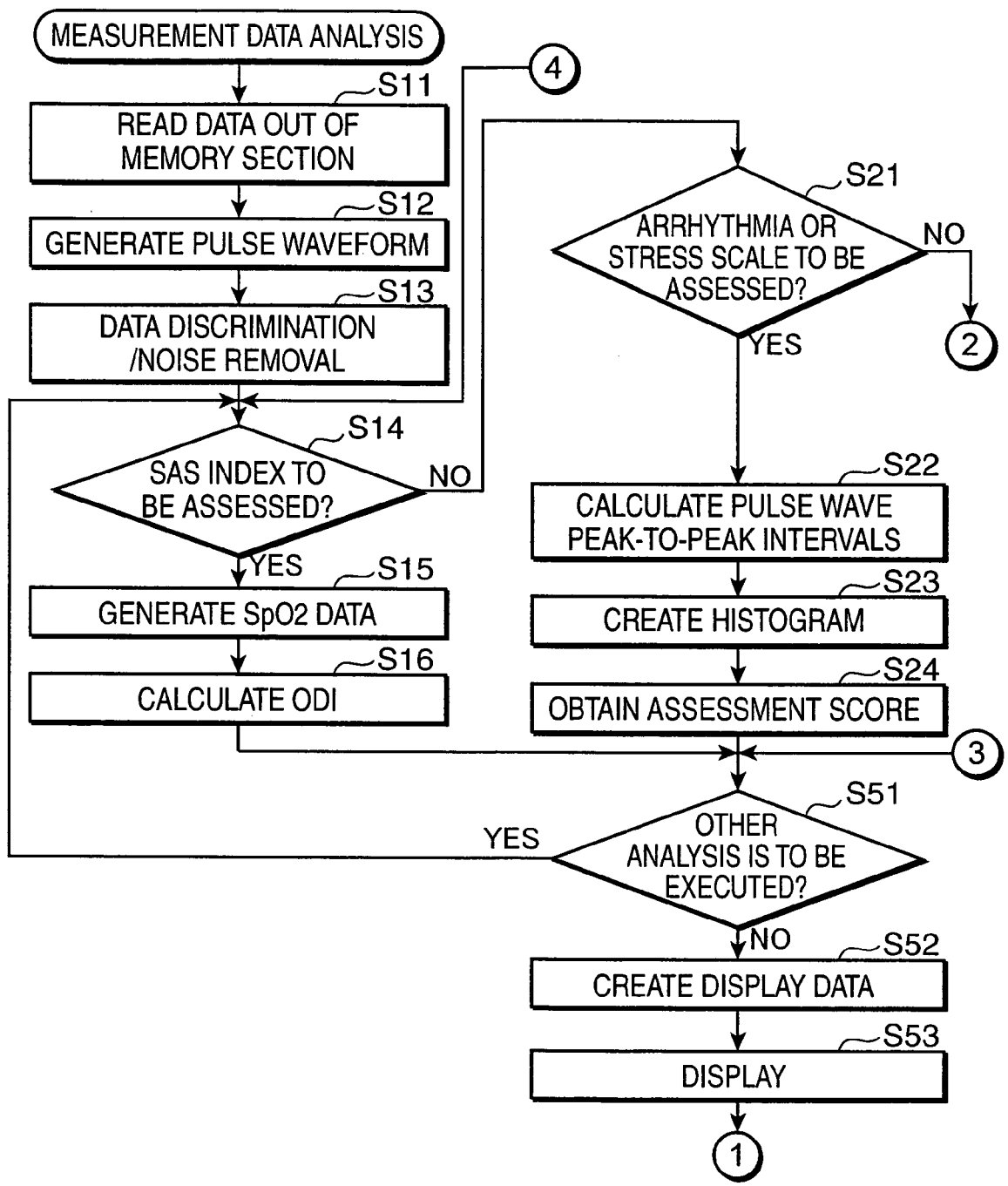
FIGS. 24 and 25 are a set of flowcharts showing details on a measurement data analysis process in Step S7 of the flowchart in FIG. 23.
Figure 25:
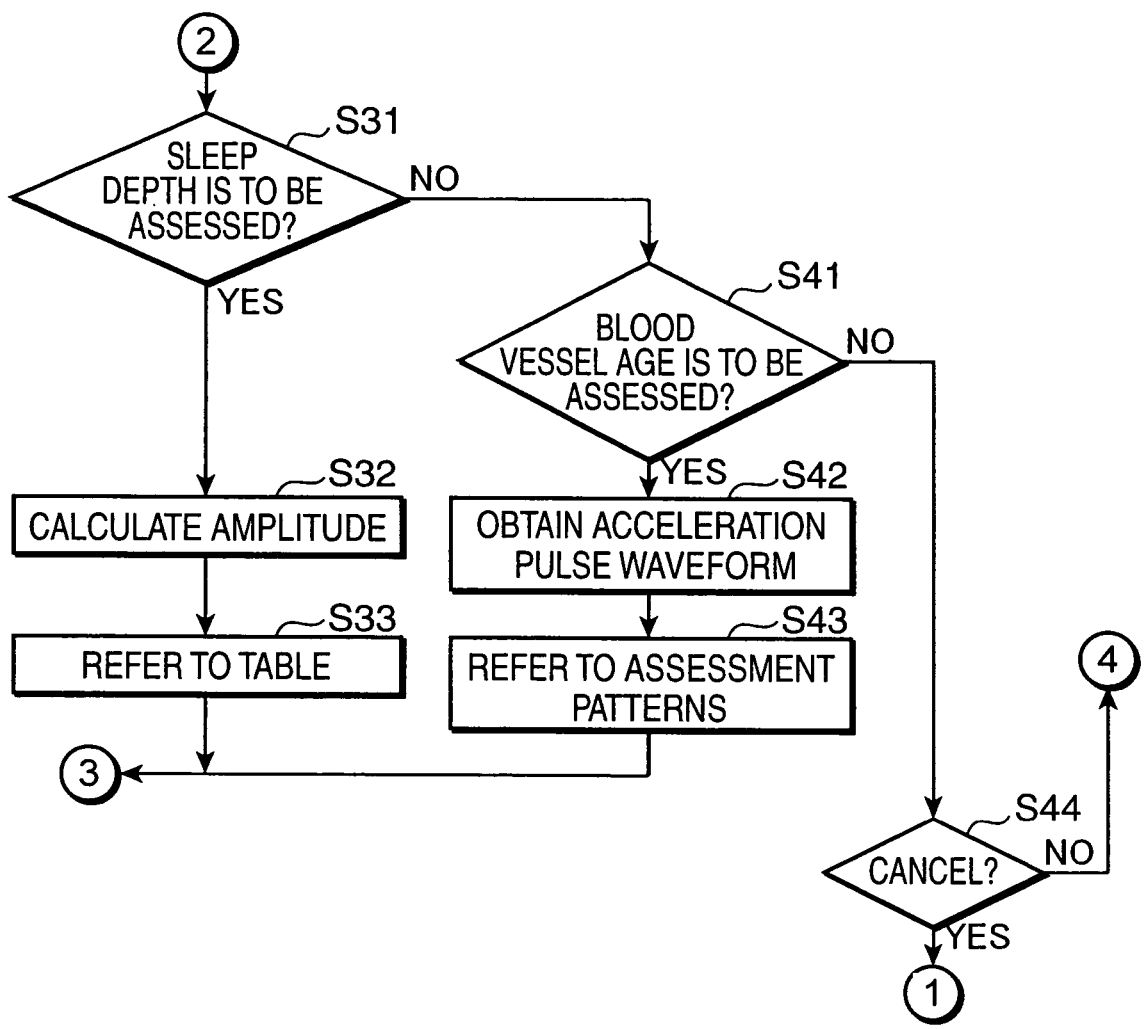

In this section, an operation of the pulse wave analyzing device S1 i.e. the pulse oximeter 20 in the embodiment is described referring to a flowchart shown in FIGS. 23 through 25. FIG. 23 is a flowchart showing an overall operation flow of the pulse oximeter 20.

First, the pulse oximeter 20 is removably attached to an appropriate site of a subject to be measured i.e. a wrist of the subject, the probe 22 is removably attached to a fingertip of the subject, the power source switch 211 (see FIG. 2) of the pulse oximeter 20 is turned on, and the measurement mode is set (Step S1). Thereafter, a measurement is started. In the case where overnight pulse oximetry or the like is executed, a timer may be set to start a measurement upon lapse of a certain time after the subject falls asleep.

When the measurement is started, it is judged whether the current time is coincident with the time of a predetermined sampling frequency (Step S2). If it is judged that the current time is coincident with the time of the sampling frequency (YES in Step S2), the probe 22 is activated to acquire 2-wavelength photoelectric pulse wave data or 1-wavelegnth photoelectric pulse wave data from the subject, and, according to needs, acquire measurement data concerning body movement information or body position information on the subject from the acceleration sensor 55 (see FIG. 3) (Step S3). Then, after an analog-to-digital conversion by the A/D converter 32 and a predetermined computation process are executed, the measurement data is stored into the memory section 51 of the device body 21 in association with time information (Step S4).

Then, it is judged whether the measurement has been completed (Step S5). If it is judged that the measurement is ongoing (NO in Step S5), the routine returns to Step S2 to repeat the operations from Step S2 to Step S5, and the measurement data is accumulated in the memory section 51. On the other hand, if it is judged that the measurement period has elapsed, or if it is judged that the subject is completely awakened during the measurement period and forcibly terminated the measurement operation (YES in Step S5), the measurement operation by the pulse oximeter 20 is ended.

Thereafter, it is judged whether an operation signal of designating execution of the analysis mode of analyzing the acquired photoelectric pulse wave data has been issued from the operating section 52 (Step S6). If it is judged that the operation signal of designating execution of the analysis mode has been issued (YES in Step S6), the measurement data i.e. the photoelectric pulse wave data stored in the memory section 51 is read out therefrom, and measurement data analysis for the various cases is conducted (Step S7).

FIGS. 24 and 25 are a set of flowcharts showing details on the measurement data analysis in Step S7 of the flowchart shown in FIG. 23. Referring to FIGS. 24 and 25, when the measurement data analysis is started, the measurement data stored in the memory section 51 is read out therefrom by the analysis processing section 43 (see FIGS. 3 and 4) (Step S11). Then, the pulse waveform generator 611 of the preprocessor 61 generates the photoelectric pulse waveform 71 as shown in FIG. 5 (Step S12). Subsequently, the data processor 612 performs a noise removal process by executing a moving averaging process with respect to the photoelectric pulse waveform 71 for instance, and performs a data discriminating process of discarding the data acquired while the subject was in a walking condition, as abnormal data, based on an axial output from the acceleration sensor 55 (Step S13).

Thereafter, the analysis controller 65 judges whether a sleep apnea index i.e. a SAS index is to be assessed (Step S14). If it is judged that the sleep apnea index is to be assessed (YES in Step S14), the $SpO_2$ data generator 621 generates the $SpO_2$ curve as shown in FIG. 6 (Step S15). Then, the ODI calculator 631 calculates an ODI by counting the number of the Dip on the $SpO_2$ curve, and by converting the counted number into the number of appearances of the Dip per hour (Step S16). The calculated ODI is temporarily stored in the memory section 51. Thereafter, the analysis controller 65 judges whether an analysis concerning a case other than the SAS is to be conducted (Step S51). If it is judged that the analysis is to be conducted (YES in Step S51), the routine returns to Step S14.

If it is judged that the SAS index is not to be assessed, including a case that the SAS index assessment has been completed (NO in Step S14), the analysis controller 65 judges whether an arrhythmia or a stress scale is to be assessed (Step S21). If it is judged that the arrhythmia or the stress scale is to be assessed (YES in Step S21), the peak-to-peak interval calculator 622 calculates pulse wave peak-to-peak intervals (Step S22), and, according to needs, generates a histogram or the like (Step S23). Then, the arrhythmia assessor 632 and/or the stress scale assessor 633 is operative to obtain a predetermined assessment score by applying the degree of variation in pulse wave peak-to-peak intervals to a predetermined index, creating a trend graph, or the like (Step S24). Thereafter, the judgment process in Step S51 is conducted again (Step S51).

On the other hand, if it is judged that the arrhythmia or the stress scale is not be assessed (NO in Step S21), it is judged whether the sleep depth is to be assessed (Step S31). If it is judged that the sleep depth is to be assessed (YES in Step S31), the amplitude calculator 623 calculates bottom-to-peak amplitude values each based on the bottom value and the peak value that appear per pulsation of the photoelectric pulse waveform (Step S32). Then, the sleep depth assessor 634 obtains an assessment score regarding the sleep depth by referring to the sleep condition assessment table, as shown in FIG. 15, in which the bottom-to-peak amplitude values and the sleep conditions are correlated to each other (Step S33). Thereafter, the judgment process in Step S51 is conducted again (Step S51).

If, on the other hand, it is judged that the sleep depth is not be assessed (NO in Step S31), it is judged whether the blood vessel age is to be assessed (Step S41). If it is judged that the blood vessel age is to be assessed (YES in Step S41), the acceleration pulse wave calculator 624 obtains an acceleration pulse waveform by a second order derivation of the photoelectric pulse waveform (Step S42). Then, the blood vessel assessor 635 obtains an assessment score relating to the blood vessel age by comparing the obtained acceleration pulse waveform with the typical acceleration pulse wave patterns as shown in FIG. 16 (Step S43). Thereafter, the judgment process in Step S51 is conducted again (Step S51).

If, on the other hand, it is judged that the blood vessel age is not be assessed (NO in Step S41), it is judged whether a cancellation signal has been issued from the operating section 52 or the like (Step S44). If it is judged that the cancellation signal has been issued (YES in Step S44), the routine returns to Step S6 in FIG. 23. If, on the other hand, it is judged that the cancellation signal has not been issued (NO in Step S44), the routine returns to Step S14 to cyclically repeat the operations.

If it is judged that no more analysis process is to be executed (NO in Step S51), the display controller 44 is operative to create predetermined display data e.g. display data for causing the display section 212 to display one of the indications as shown in FIGS. 17A through 22 (Step S52). Thereafter, the created display data is displayed on the display section in a predetermined display format (Step S53).

The invention is described in terms of the foregoing embodiment. Alternatively, various modified embodiments may be applied to the invention. In the embodiment, cases to be analyzed by the inventive pulse wave analyzing device are the sleep apnea index, the arrhythmia, the degree of stress, the sleep depth, and the blood vessel age. Alternatively, various diagnosable cases based on the pulse wave data other than the foregoing cases may be set as objects to be analyzed.

The foregoing embodiment primarily includes the following arrangements.

A pulse wave analyzing device according to an aspect of the invention comprises: a performance part for performing analyzing of a pulse wave of a living body; and a mounting member for substantially integrally mounting constituent elements of the performance part. The performance part includes: a sensor section for measuring parameters relating to the pulse wave of the living body; an A/D converter for converting a measurement signal outputted from the sensor section into a digital signal; an analysis processing section for performing a predetermined data analysis with respect to measurement data outputted from the A/D converter; and a display section for displaying predetermined information relating to the measurement, wherein the analysis processing section has a first analysis processor for performing a pulse wave analysis at least for a first case, and a second analysis processor for performing a pulse wave analysis for a second case different from the first case based on the measurement data relating to the pulse wave.

A pulse wave analyzing device according to another aspect of the invention comprises: a performance part for performing analyzing of a pulse wave of a living body; and a mounting member for substantially integrally mounting constituent elements of the performance part. The performance part includes: a sensor section for measuring parameters relating to the pulse wave of the living body; an A/D converter for converting a measurement signal outputted from the sensor section into a digital signal; an analysis processing section for performing a plurality of kinds of data analysis with respect to measurement data outputted from the A/D converter; and a display section for displaying predetermined information relating to the measurement.

In the above arrangements, not only the sensor section and the A/D converter but also the analysis processing section for performing the analysis with respect to the measurement data are integrally mounted on the mounting member of the pulse wave analyzing device. The analysis result can be displayed on the display section so that the user can be informed of the analysis result on the measurement data merely with use of the pulse wave analyzing. Also, the analysis processing section is so configured as to perform the data analyses of different kinds. In other words, at least the first analysis processor is enabled to perform the pulse wave analysis for the first case, and the second analysis processor is enabled to perform the pulse wave analysis for the second case different from the first case. This allows for providing a broad-ranging data analysis for the different cases with the single pulse wave analyzing device.

The above arrangements enable to provide a pulse wave analyzing device capable of diagnosing the plural cases by one-time measurement of the parameters relating to the pulse wave, and of displaying the analysis results promptly after the measurement. Thus, since the subject himself or herself can readily recognize the plural suspected cases, this provides enhanced convenience, and is advantageous in diagnosing both symptoms on e.g. a sleep disorder and a circulatory system disease by one-time measurement even if the subject with suspected symptoms on the sleep disorder and the circulatory system disease visits a clinic for diagnosis.

In the above arrangements, preferably, the performance part may further include: a memory section for storing therein the measurement data outputted from the A/D converter, or measurement data after the analysis by the analysis processing section; and a communication section for communicating data with another electrical device.

With the above arrangement, the measurement data that has been temporarily stored in the memory section, or the measurement data after the analysis can be transferred to the another electrical device via the communication section. This enables to perform a detailed analysis by the another electrical device e.g. a personal computer, or to construct a database.

In the above arrangements, preferably, the performance part may further include a display controller for controlling the display section to display the information, and the display controller may control the display section to selectively or simultaneously display at least an analysis result by the first analysis processor and an analysis result by the second analysis processor.

With the above arrangement, the display controller controls the display section to selectively or simultaneously display the analysis result by the first analysis processor and the analysis result by the second analysis processor depending on a condition such as an appearing manner of the case to be analyzed. This enables to provide a user-friendly pulse wave analyzing device.

In the above case, preferably, the display controller may control the display section to display the analysis result at least in a first display mode of displaying the analysis result in a first display manner, or in a second display mode of displaying the analysis result in a second display manner different from the first display manner.

With the above arrangement, the analysis result by the first analysis processor and the analysis result by the second analysis processor can be displayed on the display section in versatile display manners. Accordingly, an intended analysis result can be displayed according to needs of a user by e.g. setting the detailed display mode, the simplified display mode, the pictorial indication mode, or the like.

In any one of the above arrangements, preferably, the sensor section may include a light emitter for emitting light of two wavelengths different from each other, and a light detector for receiving the light emitted from the light emitter and transmitted through the living body, and the first analysis processor may perform the pulse wave analysis, using a 2-wavelength pulse waveform, and the second analysis processor may perform the pulse wave analysis, using a 1-wavelength pulse waveform.

With the above arrangement, the pulse waveform analyses for the various cases can be performed, using the 2-wavelength pulse waveform and the 1-wavelength pulse waveform individually, thereby increasing the number of cases to be analyzed.

In the above case, preferably, the cases to be analyzed by the analysis processing section may include two or more cases selected from the group consisting of: a sleep apnea index based on the 2-wavelength pulse waveform; an arrhythmia based on pulse wave peak-to-peak intervals, utilizing the 1-wavelength pulse waveform; a degree of stress based on the pulse wave peak-to-peak intervals; a depth of sleep based on an amplitude of the pulse waveform, and a variation in the pulse waveform; and a blood vessel age based on an acceleration pulse waveform obtained by a derivation of the pulse waveform.

With the above arrangement, data analyses on the respective cases, and diagnoses thereof can be accurately performed depending on the data analysis compatibility for the respective cases, utilizing the 2-wavelegnth pulse waveform or the 1-wavelength pulse waveform.

In the above arrangements, preferably, the performance part may have such dimensions as to be removably attached to a site near a wrist of a human body. This enables to provide a pulse wave analyzing device with enhanced fitting to the human body.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A pulse wave analyzing device comprising:
    a performance part for performing analyzing of a pulse wave of a living body; and
    a mounting member for substantially integrally mounting constituent elements of the performance part,
    the performance part including:
        a sensor section for measuring parameters relating to the pulse wave of the living body, said sensor section including at least a light emitter for emitting light of two wavelengths different from each other, and a light detector for receiving the light emitted from the light emitter and transmitted through the living body, said sensor section being configured to obtain a 2-wavelength pulse waveform by a one-time measurement as a measurement signal;
        an A/D converter for converting the measurement signal outputted from the sensor section into a digital signal;
        a memory section for storing therein measurement data including the digital signal outputted from the A/D converter;
        an analysis processing section for performing a predetermined data analysis with respect to the measurement data read out of the memory section; and
        a display section for displaying predetermined information relating to the measurement, wherein
    the analysis processing section includes a first analysis processor configured to perform at least a first pulse wave analysis, and a second analysis processor configured to perform at least a second pulse wave analysis different from the first pulse wave analysis,
    said analysis processing section being configured to perform the first and second pulse wave analyses in a manner so as to determine a degree of stress including discriminating a normal condition from a stressful condition, based on a degree of variation in pulse wave peak-to-peak intervals derived from a histogram of peak-to-peak intervals, the degree of variation for a stressful condition being lower than for a normal condition, said analysis processing section further being configured to determine one or more conditions selected from the group consisting of: a sleep apnea index, based on a 2-wavelength pulse waveform; an arrhythmia, based on pulse wave peak-to-peak intervals utilizing a 1-wavelength pulse waveform; a depth of sleep, based on an amplitude of a pulse waveform and a variation in the pulse waveform; and a blood vessel age, based on an acceleration pulse waveform obtained by a derivation of a pulse waveform.

2. The pulse wave analyzing device according to claim 1, wherein the performance part further includes:
    a communication section for communicating data with another electrical device.

3. The pulse wave analyzing device according to claim 1, wherein
    the performance part further includes a display controller for controlling the display section to display the information, and
    the display controller controls the display section to selectively or simultaneously display at least an analysis result by the first analysis processor and an analysis result by the second analysis processor.

4. The pulse wave analyzing device according to claim 3, wherein the display controller is configured to control the display section to display the analysis result at least in a first display mode of displaying the analysis result in a first display manner, or in a second display mode of displaying the analysis result in a second display manner different from the first display manner.

5. The pulse wave analyzing device according to claim 1, wherein
    the performance part has such dimensions as to be removably attached to a site near a wrist of a human body.

6. The pulse wave analyzing device according to claim 1, wherein said sensor section further includes an acceleration sensor.

7. The pulse wave analyzing device according to claim 1, wherein said analysis processing section is configured to perform one of the first or second pulse wave analyses in a manner so as to determine a sleep apnea index by analyzing a time-based change in SpO$_2$ and determining a count of dips where a SpO$_2$ value is lower than a predetermined value.

8. The pulse wave analyzing device according to claim 1, wherein said analysis processing section is configured to perform one of the first or second pulse wave analyses in a manner so as to determine an arrhythmia based on a degree in variation in pulse wave intervals.

9. The pulse wave analyzing device according to claim 1, wherein said analysis processing section is configured to determine a degree of stress by comparing a determined degree in variation in pulse wave peak-to-peak intervals to stored data which correlates variation in pulse wave peak-to-peak intervals and degrees of stress.

10. The pulse wave analyzing device according to claim 1, wherein said analysis processing section is configured to perform one of the first or second pulse wave analyses in a manner so as to determine a depth of sleep based on a time-based change in pulse wave bottom-to-peak amplitude values.

11. The pulse wave analyzing device according to claim 1, wherein said analysis processing section is configured to determine a blood vessel age by comparing said acceleration pulse waveform with a predetermined acceleration pulse waveform pattern.

12. The pulse wave analyzing device according to claim 1, wherein said analysis processing section is configured to perform each of the following analyses: determining a sleep apnea index, assessing an arrhythmia, determining a degree of stress, determining a depth of sleep, and determining a blood vessel age.

13. A pulse wave analyzing device comprising:
a performance part for performing analyzing of a pulse wave of a living body; and
a mounting member for substantially integrally mounting constituent elements of the performance part,
the performance part including:
a sensor section for measuring parameters relating to the pulse wave of the living body, said sensor section being configured to obtain a 2-wavelength pulse waveform by a one-time measurement as a measurement signal;
an A/D converter for converting the measurement signal outputted from the sensor section into a digital signal;
a memory section for storing therein measurement data including the digital signal outputted from the A/D converter;
an analysis processing section for performing a predetermined plurality of kinds of data analysis with respect to the measurement data read out of the memory section, said analysis processing section being configured to perform said plurality of kinds of data analysis in a manner so as to determine a degree of stress including discriminating a normal condition from a stressful condition, based on a degree of variation in pulse wave peak-to-peak intervals derived from a histogram of peak-to-peak intervals, the degree of variation for a stressful condition being lower than for a normal condition, and one or more conditions selected from the group consisting of: a sleep apnea index, an arrhythmia, a depth of sleep, and a blood vessel age; and
a display section for displaying predetermined information relating to the measurement.

14. The pulse wave analyzing device according to claim 13, wherein said analysis processing section is configured to analyze at least one of:
a sleep apnea index based on the 2-wavelength pulse waveform;
an arrhythmia based on pulse wave peak-to-peak intervals utilizing a 1-wavelength pulse waveform;
a depth of sleep based on an amplitude of a pulse waveform and a variation in the pulse waveform; and
a blood vessel age based on an acceleration pulse waveform obtained by a derivation of a pulse waveform.

15. The pulse wave analyzing device according to claim 13, wherein said analysis processing section is configured to analyze each of the following: a sleep apnea index, an arrhythmia, a degree of stress, a depth of sleep, and a blood vessel age.

16. The pulse wave analyzing device according to claim 13, wherein said sensor section further includes an acceleration sensor.

17. The pulse wave analyzing device according to claim 13, wherein said analysis processing section is configured to determine a blood vessel age by comparing said acceleration pulse waveform with a predetermined acceleration pulse waveform pattern.

18. The pulse wave analyzing device according to claim 13, wherein said analysis processing section is configured to perform each of the following analyses: determining a sleep apnea index, assessing an arrhythmia, determining a degree of stress, determining a depth of sleep, and determining a blood vessel age.

19. The pulse wave analyzing device according to claim 18, wherein said analysis processing section is configured to determine a degree of stress by comparing a determined degree in variation in pulse wave peak-to-peak intervals to stored data which correlates variation in pulse wave peak-to-peak intervals and degrees of stress.

20. A pulse wave analyzing device comprising:
a sensor system configured to measure parameters relating to the pulse wave of the living body, said sensor system including at least a light emitter for emitting light of two wavelengths different from each other, and a light detector for receiving the light emitted from the light emitter that has been transmitted through a portion of a living body, said sensor system being configured to obtain a 2-wavelength pulse waveform by a one-time measurement as a measurement signal;
an A/D converter for converting the measurement signal outputted from the sensor system into a digital signal;
a memory system for storing therein measurement data including the digital signal outputted from the A/D converter;
an analysis processor which is configured to perform a predetermined data analysis on the measurement data read out of the memory system, said analysis processor being configured to perform a degree of stress analysis including discriminating a normal condition from a stressful condition, based on a degree of variation in pulse wave peak-to-peak intervals derived from a histogram of peak-to-peak intervals, the degree of variation for a stressful condition being lower than for a normal condition, said analysis processor being configured to perform at least one additional analysis selected from the group consisting of: determining a sleep apnea index, assessing an arrhythmia, determining a depth of sleep, and determining a blood vessel age; and
a display system for displaying information relating to the measurement.

21. The pulse wave analyzing device according to claim 20, wherein said analysis processor is configured to perform data analysis by performing at least one of:

an analysis of sleep apnea index based on the 2-wavelength pulse waveform by analyzing a time-based change in $SpO_2$ and determining a count of dips where a $SpO_2$ value is lower than a predetermined value, an analysis of an arrhythmia based on pulse wave peak-to-peak intervals utilizing a 1-wavelength pulse waveform based on a degree in variation in pulse wave intervals, an analysis of a degree of stress based on pulse wave peak-to-peak intervals based on a degree in variation in pulse wave intervals, an analysis of a depth of sleep based on an amplitude of a pulse waveform and a variation in the pulse waveform based on a degree in variation in pulse wave intervals, and an analysis of a blood vessel age based on an acceleration pulse waveform obtained by a derivation of a pulse waveform by comparing said acceleration pulse waveform with a predetermined acceleration pulse waveform pattern.

22. The pulse wave analyzing device according to claim 21, wherein said sensor system further includes an acceleration sensor.

23. The pulse wave analyzing device according to claim 20, wherein said analysis processor is configured to perform each of the following analyses: determining a sleep apnea index, assessing an arrhythmia, determining a degree of stress, determining a depth of sleep, and determining a blood vessel age.

24. The pulse wave analyzing device according to claim 20, wherein said analysis processing section is configured to determine a blood vessel age by comparing said acceleration pulse waveform with a predetermined acceleration pulse waveform pattern.

25. A pulse wave analyzing device comprising:
a sensor system configured to measure parameters relating to the pulse wave of the living body, said sensor system including at least a light emitter for emitting light of two wavelengths different from each other, and a light detector for receiving the light emitted from the light emitter that has been transmitted through a portion of a living body, said sensor system being configured to obtain a 2-wavelength pulse waveform by a one-time measurement as a measurement signal;

an A/D converter for converting the measurement signal outputted from the sensor system into a digital signal;

a memory system for storing therein measurement data including the digital signal outputted from the A/D converter;

an analysis processor which is configured to perform a predetermined data analysis on the measurement data read out of the memory system, said analysis processor being configured to perform analyses to determine each of:

a sleep apnea index based on the 2-wavelength pulse waveform by analyzing a time-based change in $SpO_2$ and determining a count of dips where a $SpO_2$ value is lower than a predetermined value;

an arrhythmia based on pulse wave peak-to-peak intervals utilizing a 1-wavelength pulse waveform based on a degree in variation in pulse wave intervals;

a degree of stress, including discriminating a normal condition from a stressful condition, by comparing a degree in variation in pulse wave peak-to-peak intervals derived from a histogram of peak-to-peak intervals to stored data which correlates variation in pulse wave peak-to-peak intervals and degrees of stress, the degree of variation for a stressful condition being lower than for a normal condition;

a depth of sleep based on an amplitude of a pulse waveform and a variation in the pulse waveform based on a degree in variation in pulse wave intervals; and a blood vessel age, said blood vessel age being determined by comparing an acceleration pulse waveform with a predetermined acceleration pulse waveform pattern; and a display system for displaying information relating to the measurement.

* * * * *